(12) United States Patent
Brenneman et al.

(10) Patent No.: US 8,273,095 B2
(45) Date of Patent: Sep. 25, 2012

(54) DEVICE AND METHOD FOR ESTABLISHING AN ARTIFICIAL ARTERIO-VENOUS FISTULA

(75) Inventors: Rodney A. Brenneman, San Juan Capistrano, CA (US); J. Christopher Flaherty, Topsfield, MA (US); Dean Schaefer, Aliso Viejo, CA (US); Peter Davis, Dana Point, CA (US); Brad Kellerman, Escondido, CA (US)

(73) Assignee: ROX Medical, Inc., San Clemente, CA (US)

( * ) Notice: Subject to any disclaimer, the term of this patent is extended or adjusted under 35 U.S.C. 154(b) by 693 days.

(21) Appl. No.: 12/502,120

(22) Filed: Jul. 13, 2009

(65) Prior Publication Data

US 2009/0275876 A1 Nov. 5, 2009

Related U.S. Application Data

(60) Division of application No. 11/696,635, filed on Apr. 4, 2007, now Pat. No. 7,828,814, which is a continuation-in-part of application No. 11/356,876, filed on Feb. 17, 2006, which is a continuation-in-part of application No. 10/927,704, filed on Aug. 27, 2004, now abandoned.

(51) Int. Cl.
A61B 17/08 (2006.01)
A61M 5/00 (2006.01)
(52) U.S. Cl. ............... 606/151; 606/153; 604/8
(58) Field of Classification Search ...... 604/8; 606/151, 606/153; 623/23.72
See application file for complete search history.

(56) References Cited

U.S. PATENT DOCUMENTS

| | | | |
|---|---|---|---|
| 3,538,917 A | 11/1970 | Selker | |
| 3,675,656 A | 7/1972 | Hakim | |
| 3,730,186 A | 5/1973 | Edmunds, Jr. et al. | |
| 3,882,862 A | 5/1975 | Berend | |
| 4,586,501 A | 5/1986 | Claracq | |
| 4,601,718 A | 7/1986 | Possis et al. | |
| 4,828,544 A | 5/1989 | Lane et al. | |
| 5,108,420 A | 4/1992 | Marks | |
| 5,258,042 A | 11/1993 | Mehta | |
| 5,491,224 A | 2/1996 | Bittner et al. | |
| 5,507,725 A | 4/1996 | Savage et al. | |
| 5,756,696 A | 5/1998 | Gray et al. | |
| 5,830,222 A | 11/1998 | Makower | |
| 5,830,224 A | 11/1998 | Cohn et al. | |
| 5,843,170 A | 12/1998 | Ahn | |

(Continued)

FOREIGN PATENT DOCUMENTS

EP 1614400 A2 1/2006

(Continued)

OTHER PUBLICATIONS

"Causes of Erectile Dysfunction", eMedicine Health website, 2008, http://www.emedicinehealth.com/causes_of_erectile_dysfunction/page3_em.htm.

(Continued)

*Primary Examiner* — Leslie Deak
*Assistant Examiner* — Susan Su
(74) *Attorney, Agent, or Firm* — Levine Bagade Han LLP

(57) ABSTRACT

A shunt rivet for implantation in the aorta and inferior vena cava to treat chronic obstructive pulmonary disease, and a method of treating chronic obstructive pulmonary disease.

12 Claims, 19 Drawing Sheets

U.S. PATENT DOCUMENTS

| | | | |
|---|---|---|---|
| 6,053,891 A | 4/2000 | DeCampli | |
| 6,099,542 A | 8/2000 | Cohn et al. | |
| 6,120,534 A | 9/2000 | Ruiz | |
| 6,152,937 A | 11/2000 | Peterson et al. | |
| 6,168,620 B1 | 1/2001 | Kerr | |
| 6,174,681 B1 | 1/2001 | Halling et al. | |
| 6,193,734 B1 * | 2/2001 | Bolduc et al. | 606/153 |
| 6,231,587 B1 * | 5/2001 | Makower | 606/198 |
| 6,309,415 B1 * | 10/2001 | Pulnev et al. | 623/1.22 |
| 6,376,188 B1 | 4/2002 | Halling et al. | |
| 6,391,036 B1 * | 5/2002 | Berg et al. | 606/151 |
| 6,451,048 B1 | 9/2002 | Berg et al. | |
| 6,579,311 B1 | 6/2003 | Makower | |
| 6,616,675 B1 | 9/2003 | Evard et al. | |
| 6,669,709 B1 | 12/2003 | Cohn et al. | |
| 6,695,878 B2 | 2/2004 | McGuckin, Jr. et al. | |
| 6,746,426 B1 | 6/2004 | Flaherty et al. | |
| 6,746,464 B1 | 6/2004 | Makower | |
| 6,926,690 B2 | 8/2005 | Renati | |
| 6,979,351 B2 | 12/2005 | Forsell et al. | |
| 7,011,094 B2 | 3/2006 | Rapacki et al. | |
| 7,056,326 B2 | 6/2006 | Bolduc et al. | |
| 7,316,706 B2 | 1/2008 | Bloom et al. | |
| 7,780,686 B2 * | 8/2010 | Park et al. | 606/153 |
| 2002/0189727 A1 | 12/2002 | Peterson | |
| 2003/0088256 A1 | 5/2003 | Conston et al. | |
| 2003/0100920 A1 | 5/2003 | Akin et al. | |
| 2004/0087997 A1 | 5/2004 | Brenneman | |
| 2004/0249334 A1 | 12/2004 | Cull | |
| 2004/0249335 A1 | 12/2004 | Faul et al. | |
| 2005/0049675 A1 | 3/2005 | Wallace | |
| 2005/0107733 A1 | 5/2005 | Faul et al. | |
| 2005/0124892 A1 | 6/2005 | Weitzel et al. | |
| 2005/0228402 A1 | 10/2005 | Hofmann | |
| 2006/0047337 A1 | 3/2006 | Brenneman | |
| 2006/0129083 A1 | 6/2006 | Brenneman et al. | |
| 2006/0206123 A1 | 9/2006 | Brenneman | |
| 2006/0293701 A1 | 12/2006 | Ainsworth et al. | |
| 2007/0249985 A1 | 10/2007 | Brenneman et al. | |

FOREIGN PATENT DOCUMENTS

| | | |
|---|---|---|
| WO | WO 01/05463 | 1/2001 |
| WO | WO 2006/026279 | 3/2006 |
| WO | WO 2006/066210 | 6/2006 |
| WO | WO 2007/005386 | 1/2007 |
| WO | WO 2007/014283 | 2/2007 |

OTHER PUBLICATIONS

"Chronic Obstructive Pulmonary Disease (COPD) Fact Sheet (Chronic Bronchitis and Emphysema)", Feb. 16, 2007, American Lung Association website, www.lungusa.org/site/pp.asp?e=dvLUK9O0E&b=35020.

"COPD: How is COPD Treated?", Feb. 16, 2007, National Heart Lung and Blood Institute Diseases and Conditions Index website, www.nhlbi.nih.gov/health/dci/Diseases/Copd/Copd_Treatments.html.

"Lung—Treatment of COPD and Asthma", Feb. 16, 2007, NLHEP website, www.nlhep.org/lung.trtmnt.html.

Ruebben et al., "Arteriovenous fistulas induced by femoral arterial catheterization: percuntaneous treatment," *Radiology*, 209:729, 1998.

Schlensak et al., "Pulmonary Artery Banding with a Novel Percuntaneously, Bidirectionally Adjustable Device," *Eur. J. of Cardio-thoracic Surg.*, pp. 931-933, 1997.

* cited by examiner

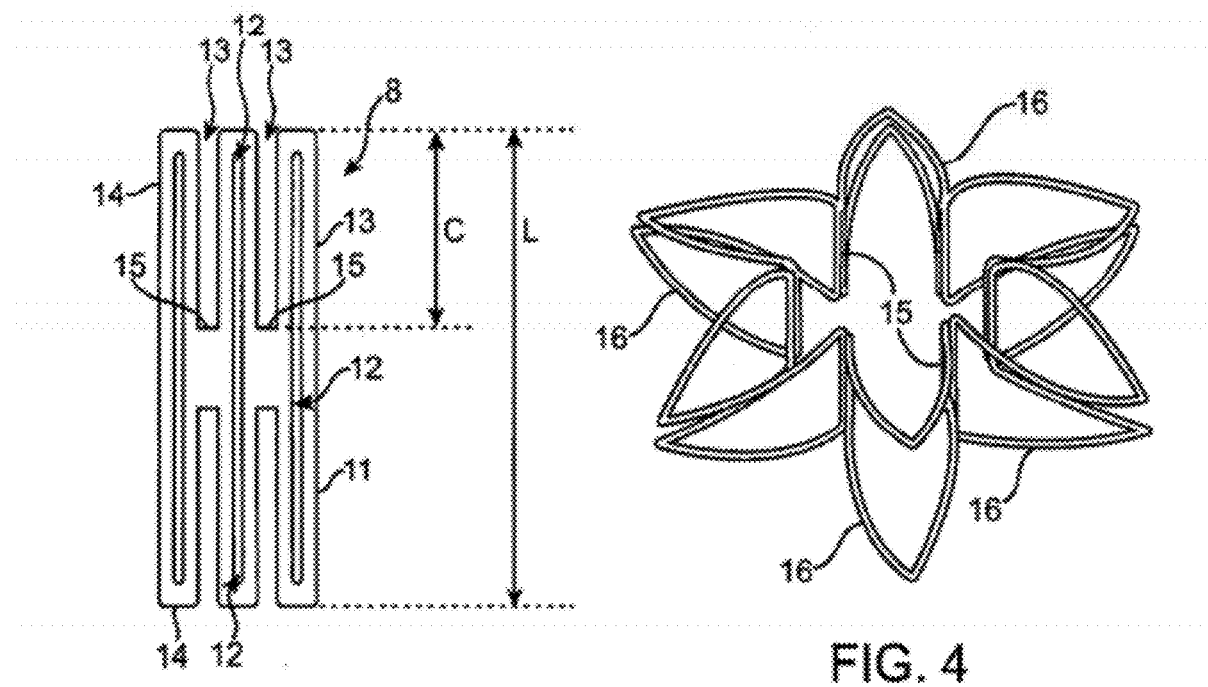
FIG. 2
FIG. 4
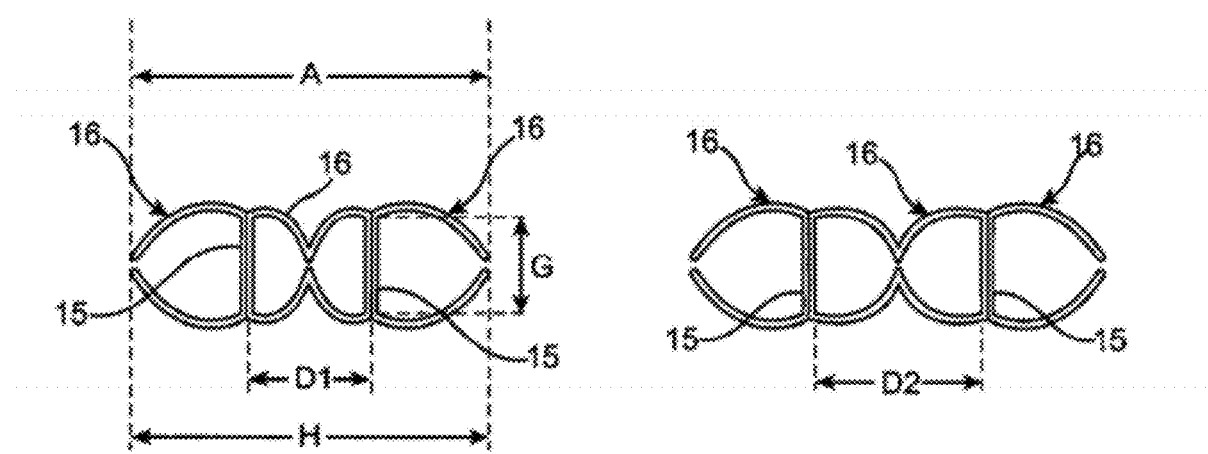
FIG. 3
FIG. 5

DEVICE AND METHOD FOR ESTABLISHING AN ARTIFICIAL ARTERIO-VENOUS FISTULA

CROSS-REFERENCE TO RELATED APPLICATIONS

This application is a divisional of U.S. application Ser. No. 11/696,635 filed Apr. 4, 2007 which is a continuation-in-part of U.S. application Ser. No. 11/356,876 filed Feb. 17, 2006, which is a continuation-in-part of U.S. application Ser. No, 10/927,704 filed Aug. 27, 2004, each of which is incorporated herein by reference in its entirety.

FIELD OF THE INVENTION

The inventions described below relate to treatments for pulmonary hypertension and vascular surgery.

BACKGROUND OF THE INVENTION

Chronic obstructive pulmonary disease (COPD), chronic hypoxia, hypertension, and left ventricular hypertrophy and pulmonary hypertension are diseases of the cardiopulmonary system. Chronic obstructive pulmonary disease (COPD), which includes chronic bronchitis and emphysema, is a slowly progressive lung disease caused primarily by smoking. In COPD, the lungs are damaged and the airways are partly obstructed, making it difficult to breath and leading to a gradual loss of lung function. Symptoms of COPD include chronic cough, excessive sputum production, low blood oxygen levels and severe disabling shortness of breath, COPD represents the fourth leading cause of death in the United States. Chronic hypoxia (reduction of oxygen supply to the body despite adequate blood flow through the body), hypertension, and left ventricular hypertrophy are related conditions which may be symptomatic of COPD or coincident with COPD.

These serious conditions affect many people, and the primary treatments are merely ameliorative. The primary treatments for COPD include avoidance of irritants such as tobacco smoke and breathing supplemental oxygen. In advanced cases of COPD, lung reduction surgery is sometimes performed, but it is not clear that it helps. There is no known cure for COPD.

An aortocaval fistula (ACF) is a rare clinical condition that can be either spontaneous (80% of the cases), related to abdominal aortic aneurysm, or the result of some trauma such as lumbar disk surgery. It is currently seen as a defect that should be cured with surgery and, possibly, stem-graft implantation in the aorta.

Contrary to this understanding, an intentionally formed aortocaval fistula appears to be a viable treatment for COPD. Recently, in our co-pending U.S. patent application Ser. No. 10/820,169 fried Apr. 6, 2004, entitled Implantable Arteriovenous Shunt Device and listing John L. Faul, Toshihiko Nishimura, Peter N. Kao & Ronald G. Pearl as inventors (the entirety of which is hereby incorporated by reference), we propose creation of an artificial aortocaval fistula as a treatment for COPD, and we disclose the method of creating the fistula and an implantable shunt for maintaining the aortocaval fistula.

Shunts or stents for connecting blood vessels have been proposed for the treatment of coronary artery disease. Makower, Device, System And Method For Interstitial Transvascular Intervention, U.S. Pat. No. 6,746,464 (Jun. 8, 2004) (filed Oct. 28, 1998) discloses a stent with a short tubular section spanning the thickness of a coronary artery and an adjacent parallel coronary vein. This stent includes "clovers" on either end of the stent, and these clovers fold radially outwardly to obstruct movement of the stent through the vessel walls. Two clovers on the proximal end of the stent are orthogonal (relative to the radial cross section of the stent) to two clovers on the distal end of the stent, and the interconnecting wires are parallel to the longitudinal axis of the device.

SUMMARY OF THE INVENTION

The devices and methods described below provide for treatment of COPD, hypertension (e.g., pulmonary hypertension, cardiac hypertension, etc.), and left, ventricular hypertrophy, and chronic hypoxia. A vascular shunt rivet is disclosed which serves to hold contiguous points of the patient's aorta and inferior vena cava (or other arteries and there associated veins, such as the femoral artery and femoral vein, or the carotid artery and the carotid vein) together and maintain an open flow path from the aorta to the vena cava. The device functions as a rivet holding the two vessel walls in close proximity, and as a shunt, permitting and maintaining flow from one blood vessel to the other. The device is implanted, between the aorta and inferior vena cava, as a treatment for pulmonary hypertension, COPD and chronic hypoxia.

The shunt rivet is provided in the form of an expandable wire frame structure adapted for transcutaneous delivery and deposit at the desired implantation site. The wire frame structure may be compressed into a small diameter configuration to fit within the distal tip of a delivery catheter. Upon expulsion from the catheter, the wire frame structure resiliently or pseudoelastically expands into a flow-through rivet comprising a tube with expanded heads at either end. When the rivet is released within an artificial fistula formed through the aorta and vena cava walls, it expands to trap the walls between the two expanded heads. The tubular section between the two expanded head may resiliently expand, and may also be balloon-expanded or otherwise plastically deformed to enlarge the flow-through lumen of the tubular section.

BRIEF DESCRIPTION OF THE DRAWINGS

FIG. 2 illustrates an aortocaval shunt rivet in its restrained condition.

FIG. 3 illustrates the aortocaval shunt rivet of FIG. 2 in a resiliently expanded configuration.

FIG. 4 is a perspective view of the aortocaval shunt rivet of FIG. 2 in a resiliently expanded configuration.

FIG. 5 illustrates the aortocaval shunt rivet of FIG. 2 in a fully expanded configuration.

DETAILED DESCRIPTION OF THE INVENTION

Figure 1:
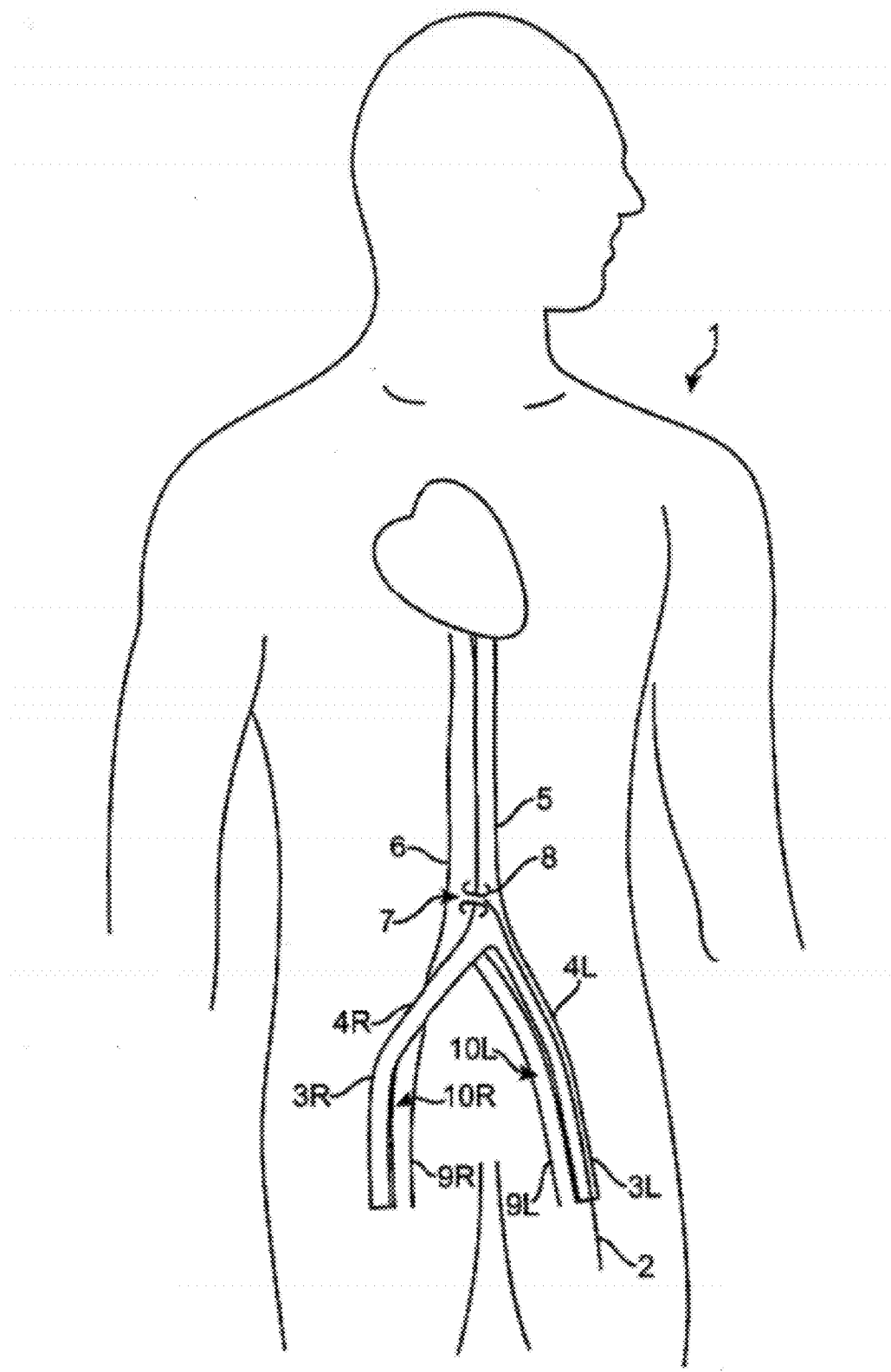
FIG. 1 illustrates the method of installing the shunt rivet to create and maintain an artificial aortocaval fistula.

FIG. 1 illustrates the method of installing the shout rivet to create and maintain an artificial aortocaval fistula. The patient 1 is shown with a delivery catheter 2 inserted into the left femoral artery/external femoral artery 3L and pushed upwardly through the left common iliac artery 4L to a point just above the aortic/iliac bifurcation in the distal abdominal aorta 5. The inferior vena cava 6 runs parallel to the aorta, and typically is contiguous with the aorta. As shown in the illustration, the left femoral artery provides a nearly straight pathway to a suitable site of the artificial aortocaval fistula 7 within the abdominal aorta (the right femoral vein 9R also provides a straight pathway to the same site on the vena cava side, and may be also be used as an access pathway). The fistula is created by forming a small hole or slit through the walls of both the aorta and the vena cava at immediately adjacent sites, and is maintained by inserting the shunt rivet 8 described below. The device may also be implanted via a route through the left femoral vein 9L, or through the right femoral artery 3R and/or right common iliac artery 4R, though these pathways are not expected to be so readily navigable. The shunt rivet may also be installed in an artificial arterio-venous fistula formed between the femoral, vein and femoral artery on either side of the body, indicated as items 10R and 10L, or between the iliac artery and the femoral vein, and at locations in the aorta above the renal arteries.

FIG. 2 illustrates the aortocaval shunt rivet 8 in its restrained condition, while FIG. 3 illustrates the aortocaval shunt rivet of FIG. 2 in its resiliency expanded configuration. The shunt rivet may be formed from a single tube 11 of resilient material, such as nitinol, spring steel, glass or carbon composites or polymers, or pseudoelastic (at body temperature) material such as nitinol or comparable alloys and polymers, by laser cutting several closed-ended slots 12 along the length of the tube (leaving the extreme distal and proximal edges of the tube intact) and cutting open-ended slots 13 from the longitudinal center of the tube through the distal and proximal edges of the tube. The open-ended slots are cut between each pair of closed-end slots to form a number of loops 14 joined at the center section by waist segments 15. Though the shunt rivet illustrated in these figures can be made of several loops of wire welded together at the waist section, and many other fabrication techniques, manufacture from a single tube as illustrated has been convenient.

After the tube is cut as described above, it is formed into its eventual resiliently expanded configuration illustrated in FIG. 3. In this configuration, the loops turn radially outwardly from the center section, and evert toward the center plane of the center section, thus forming clinch members 16 in the form of arcuate, everted, petaloid frames at either end of the loop, extending from the generally tubular center section formed by the waist segments 15. For clarity, the term everted is used here to mean that the arc over which the petaloid frame runs is such that the inside surface of the device as configured in FIG. 2 faces radially outwardly from the cylinder established by the tube. FIG. 4 is a perspective view of the shunt rivet in the resiliency expanded configuration illustrated in FIG. 3, more clearly illustrating the relationship between the several petaloid frames at each end of the shunt rivet.

FIG. 5 shows a side view of the aortocaval shunt rivet of FIG. 2 in a fully expanded configuration. Even after the device has resiliently expanded to the extent possible given its impingement upon the walls of the aorta and the vena cava, the center section may be further expanded by plastic deformation. This may be accomplished by inflating a balloon within the center section, inflating the balloon, and expanding the center section beyond its elastic or super/elastic deformation range. By plastically deforming the center section of the shunt rivet, the center section becomes more rigid and able to withstand the compressive force of the walls of the aorta and vena cava.

As illustrated, the construction provides several pairs of longitudinally opposed (that is, they bend to come into close proximity to each other, and perhaps but not necessarily, touch) and aligned (they are disposed along the same longitudinal line) distal and proximal petaloids. Overall, the petaloid frames of the distal section form a "corolla" (analogous to the corolla of a flower) flange or rivet clinch, which impinges on the vena cava wall and prevents expulsion into the aorta, and the petaloid frames of the proximal section form a corolla, flange or rivet clinch (this clinch would be analogous to a rivet head, but it is formed like the clinch after insertion of the rivet), which impinges on the aorta wall and prevents the expulsion of the shunt rivet into the vena cava, and the central section 17 forms a short length of rigid tubing to keep the fistula open. The resilient apposition of the two distal and proximal flanges or corollas so formed will securely hold the shunt rivet in place by resiliently clamping the walls of the aorta and vena cava (even over a considerable range of wall thickness or "grip range").

Referring to FIGS. 2 through 5, the shunt rivet may be manufactured with an overall initial length L of about 8 to 10 mm to obtain a grip range G of about 3 mm (given a typical aortic wall thickness of 2 mm and a typical inferior vena cava wall thickness of 1 mm at the target site), a clinch allowance C of at least about 3 mm (the clinch allowance is the distally protruding portion of a rivet that is turned over, curled or flattened to form the formed head), a formed or blind head allowance A of about 10-16 mm (we use the term blind head to refer to the distal head, which is the head that is formed on the blind side of the joint), a head diameter H of 5-16 mm, an initial shank diameter D1 of 3-8 mm (in the resiliently expanded configuration, prior to plastic deformation), a final shank diameter D2 of 5-12 mm to create a flow through lumen of about 5-10 mm diameter. The grip strength of the shunt rivet should provide for a slight compressive force exerted by the opposing clinch members on the intervening blood vessel walls. Thus, the shunt rivet is formed such that, in the resiliently expanded configuration, produces a grip strength in the range of 0.1 to 1.5 oz (about 3 to 45 gram-force) per clinch member upon the intervening blood vessels of the expected thickness.

Figure 6:
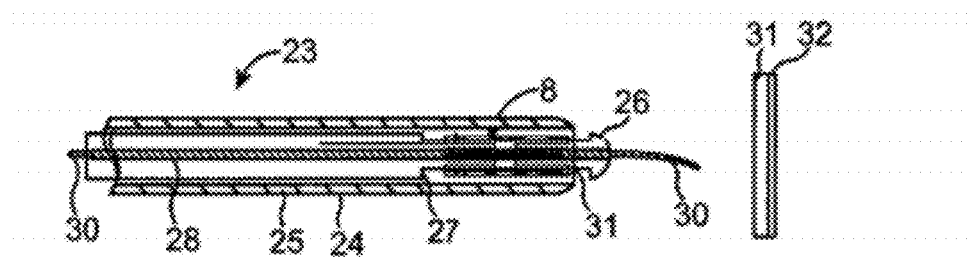
FIGS. 6 through 11 illustrate the deployment of the aortocaval shunt rivet of FIG. 2.

FIGS. 6 through 11 illustrate the method of releasing the shunt rivet so that the distal clinch members are released within the vena cava and the proximal clinch members are released within the aorta. Prior to insertion of the delivery catheter, the surgeon performing the implantation will image the aorta and inferior vena cava with appropriate fluoroscopic, ultrasonic, or other imaging methods, and create a pilot hole in the vessel walls with a crossing catheter. As shown in FIG. 6, the shunt rivet is housed within the distal tip of a delivery catheter 23, and is entirely restrained within the delivery catheter. The delivery catheter includes an outer sheath 24, a shaft 25 which is longitudinally slidable within the outer sheath, and a tapered or rounded tip 26 disposed on the shaft. The tapered may be mounted on a separate shaft, slidably disposed within the shaft 25, so that it may be pushed through the prepared aperture while holding the remainder of the device steady within the aorta. The distal edge of the outer sheath may also be rounded or tapered, as shown. A distally facing shoulder 27 on the shaft, just proximal to the shunt rivet, serves to keep the shunt rivet in place longitudinally as the outer sheath is withdrawn. A guide wire lumen 28 may be provided in the shaft for use with a guide wire 29, and may extend to the proximal end of the shaft for over-the-wire operation or may exit the shaft just proximal to the shunt rivet holding segment for monorail guidewire operation, and other guide wire configurations may also be used. A balloon 30 may be disposed on the shaft (and a suitable balloon inflation lumen provided in the shaft, and a suitable inflation pressure source in fluid communication with the lumen).

Figure 7:
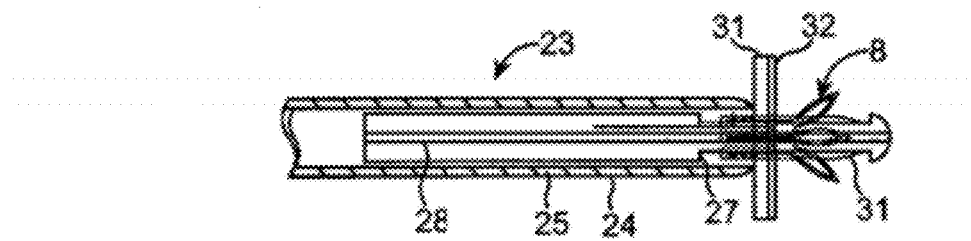
Figure 8:
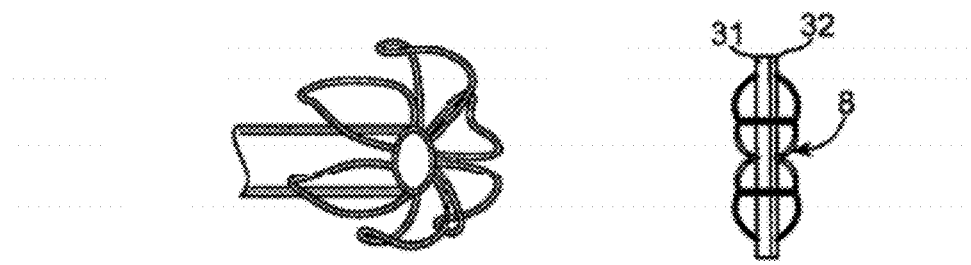

As shown in FIG. 7, the distal tip of the delivery catheter is pushed through a small aperture in the walls of the aorta and vena cava (items 31 and 32) (the aperture is made by the operator, using a separate or integral punch, needle or lance) to create the artificial aortocaval fistula. After the distal tip has entered the vena cava, the outer sheath is pulled proximally to release the distal petaloids, as shown in FIG. 8. After the distal petaloids have reverted to their unrestrained configuration, the entire device is polled proximally to seat the distal petaloids against the inner wall of the vena cava. Prior to complete release of the shunt rivet, the operator should confirm that its location is acceptable (any suitable imaging technique may be used). To allow retraction in case the shunt rivet must be repositioned, a hook 33 protrudes radially from the shaft 25 and passes through a loop of the shunt rivet. This traps and secures the shunt rivet within the outer sheath 24 until the outer sheath is moved proximally to release the proximal clinch members, so that the operator may pull the shunt rivet back into the outer sheath in case its location, as visualized prior to complete release of the shunt rivet, is undesirable. Any other retaining means, such as a resilient or spring-loaded detent, a retractable pawl which engages a loop of the shunt rivet, of a retractable hook extending inwardly from the outer sheath, may be used in place of the illustrated hook.

Figure 9:
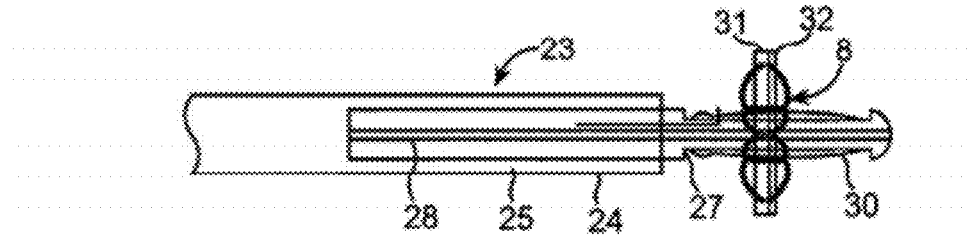
Figure 10:
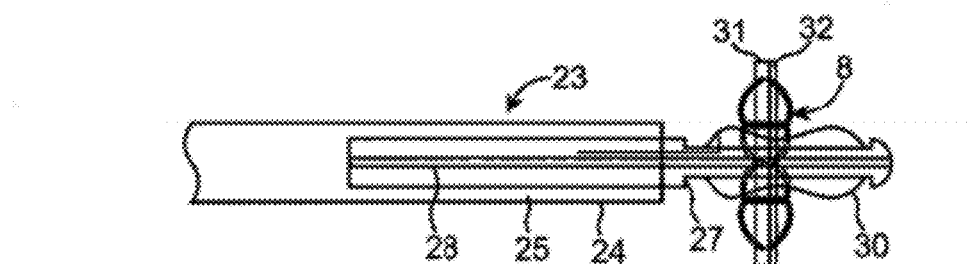
Figure 11:
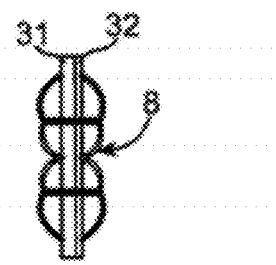

Then the outer sheath is pulled further proximally to release the proximal petaloids, as shown in FIG. 9. With the shunt rivet securely set in the artificial fistula, the center section may then be expanded by inflating the balloon as shown in FIG. 10. Upon withdrawal of the shaft, the shunt rivet remains in place to hold the two perforations in the blood vessel wall in apposition to each other to maintain the fistula, and to maintain an open shunt pathway between the aorta and vena cava, as shown in FIG. 11.

The final form of the shunt rivet is, according to the above description, accomplished with the method that includes forming the generally tubular structure having a central section with a first diameter, a proximal clinch section defined by one or more clinch members, and a distal clinch section defined by one or more clinch members, training the proximal and distal clinch members to make them resiliently biased to bend radially outwardly from the central section; then resiliently compressing the tubular structure to maintain a generally tubular shape and restraining the compressed tubular structure in a compressed configuration suitable for percutaneous insertion into the body; inserting the structure through apposing apertures in the aorta wall and vena cava wall of a patient such that the distal clinch members protrude into the vena cava of the patient and the central section is disposed within the apertures; and then releasing the distal clinch members to permit resilient expansion of the distal clinch members followed by expanding the central section through plastic deformation to larger diameter and releasing the proximal clinch members to permit resilient expansion of the proximal clinch members (the proximal clinch members may be released before or after expansion of the central section).

Figure 12:
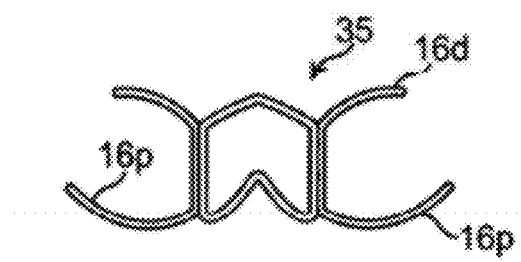
FIG. 12 illustrates an aortocaval shunt rivet with asymmetrically shaped distal and proximal flanges.
Figure 13:
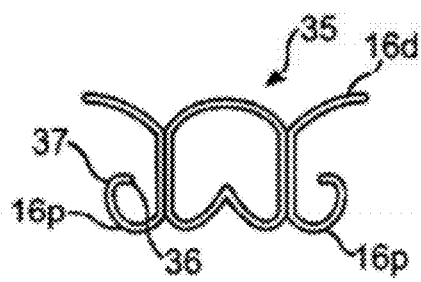
FIG. 13 illustrates an aortocaval shunt rivet with asymmetrically shaped distal and proximal flanges.

The shunt rivet illustrated above may be modified as shown in FIGS. 12 and 13, which show an aortocaval shunt rivet with asymmetrically shaped distal and proximal flanges. In FIG. 12, the shunt rivet 35 is similar to the shunt rivet of FIGS. 2 through 4, and includes the central section, the distal flange comprised of multiple petaloid wire-frame members 16*d*, and the proximal flange comprised of multiple petaloid wire-frame members 16*p*. In this embodiment, the distal corolla is horn-shaped, "salverform" or "funnelform" (as those terms are used in botany), with the petaloids arcing outwardly without everting (without a substantial arc in the proximal direction), while the proximal corolla is perianth-like, arcing outwardly and everting with a substantial arc in the distal direction. Each petaloid is significantly reflexed, like the perianth of a narcissus cyclamineus. FIG. 13 illustrates another embodiment of the aortocaval shunt rivet with asymmetrically shaped distal and proximal flanges. In FIG. 13, the proximal petaloids are highly reflexed, and evert to form pigtails with an arc of over 180°, and preferably, as illustrated, an arc in excess of about 270°, such that the proximal petaloids bend radially inwardly toward the tips 36 to present a length of wire 37, rather than the tip of the petaloids, for impingement on the blood vessel wall. One or both of the distal or proximal petaloids/clinch members may be modified to form the pigtails illustrated in FIG. 13. In the embodiments shown, the petaloids are gamopetalous (with the petals united by their margins, at least at the base, as in FIG. 2 et seq.), but they may also be polypetalous as shown below FIGS. 14, 15 and 16. The embodiments shown are also actinomorphic, though they may be constructed in zygomorphic fashion with asymmetrical petaloids.

Figure 14:
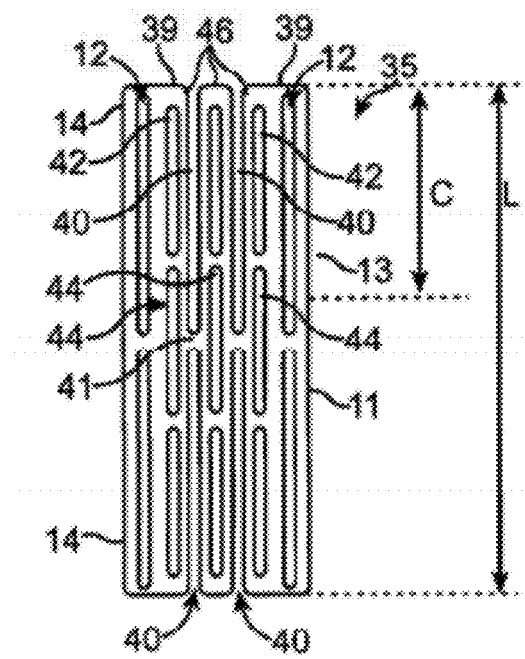
FIGS. 14, 15 and 16 illustrate an aortocaval shunt rivet with strut members that form diamond-shaped cells in the central section upon expansion.
Figure 15:
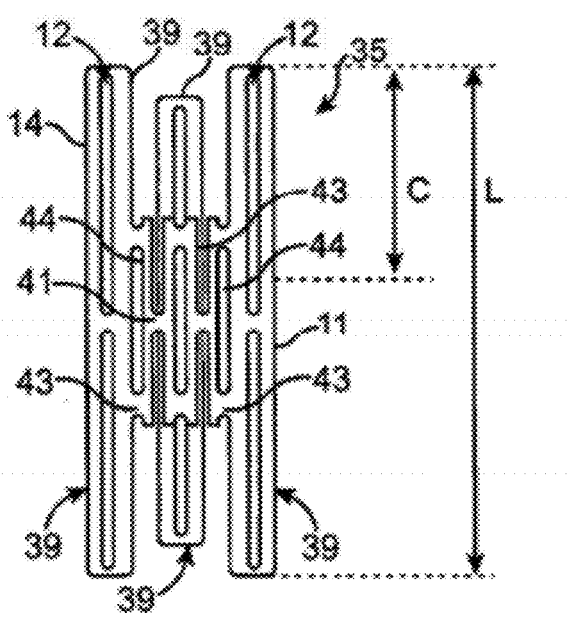
Figure 16:
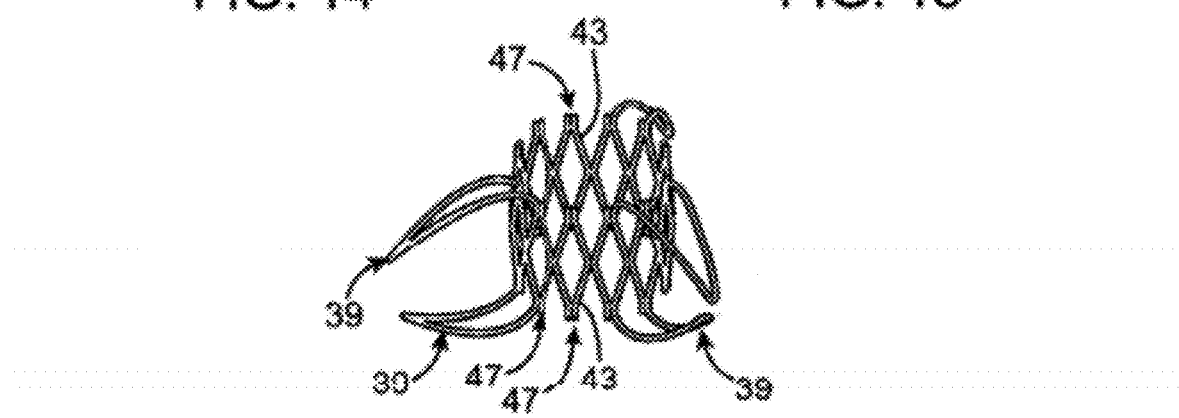

FIGS. 14, 15 and 16 illustrate an aortocaval shunt rivet 8 with diamond shaped strut members in the central section. This shunt rivet provides a central section 17 with a series of expandable loops joined by circumferentially oriented struts 38. FIG. 14 illustrates a tube 11 with numerous slots cut into it to form the shunt rivet shown in FIG. 16. Slots 12 are closed-end slots, leaving a loop 14 extending from the central section 17 to form a clinch member cell 39. Slots 40 are open or closed-end slots extending from the center of the device, leaving small circumferential struts 41 connecting adjacent cells of the device. Slots 42 are open or closed-end slots extending from the center section of the device, leaving larger waist sections 43 connecting the circumferential struts with adjacent clinch member cells of the device. Slots 44 are closed-end slots extending through the waist sections. As shown in FIG. 15, some waste area (segments intended to be removed) 46 shown in FIG. 14 are cut away and discarded, leaving expandable waist section cells 47 and clinch cells 39, interconnected by the circumferential struts 38. Though the device is illustrated with three clinch members on each end, the number of clinch members formed in the shunt rivet may be varied. The waist section cells and clinch member cells, can, as shown at 48 share struts which define contiguous cells. As shown in FIG. 16 the waist section cells, when expanded, form the diamond shaped cells of the central section. The clinch member cells comprise petaloid cells which may be described as lanceolate (narrow and tapering to an apex (though the apex is preferably blunt)), or ovate (having a broad base and narrow tip) rather than reniform or orbicular. The tip of the petaloid is preferably obtuse, rounded or blunt. As can be appreciated from FIG. 16 the clinch members may also be described as longitudinally extending wires which connect the longitudinally tips of adjacent waist section cells.

Figure 17:
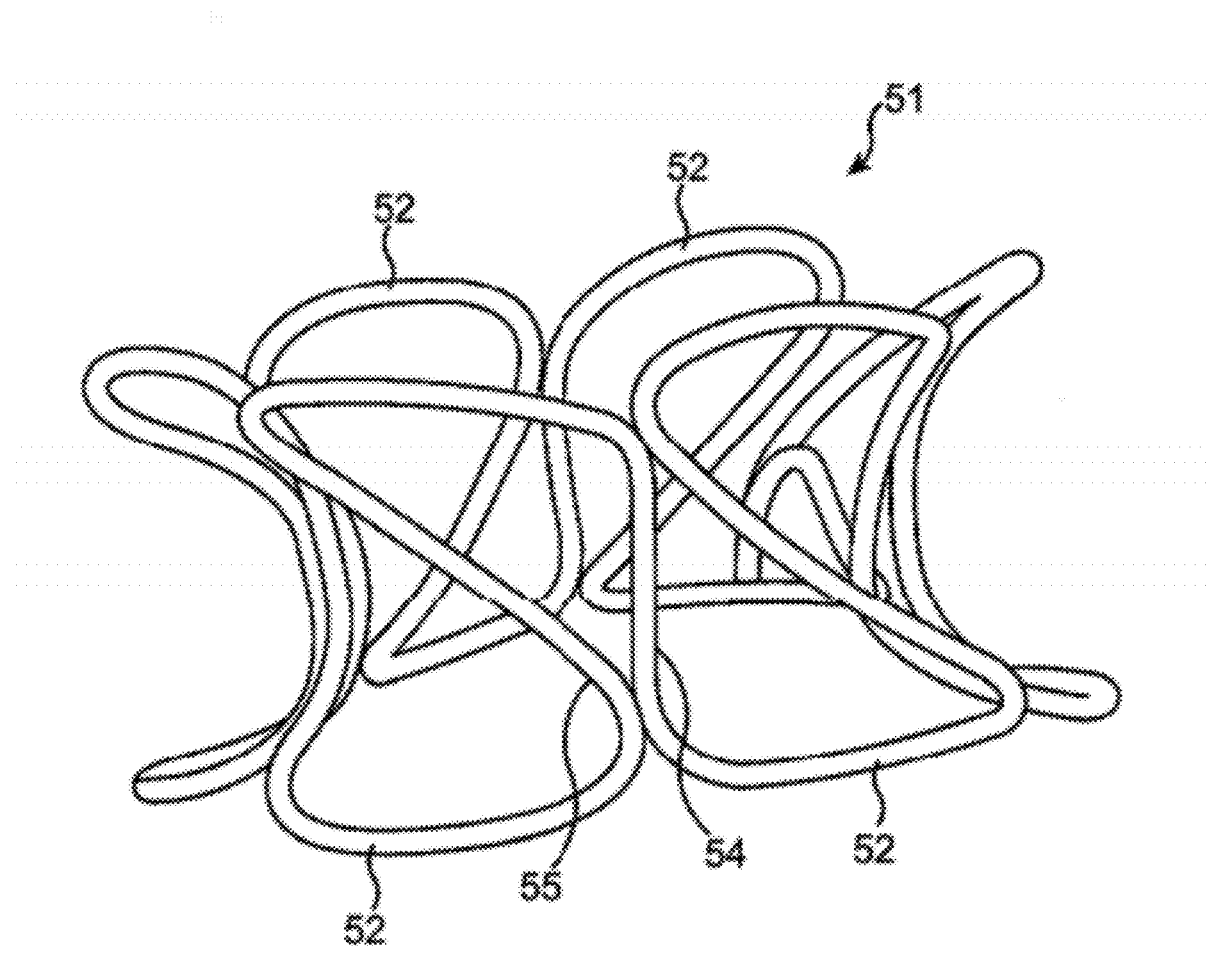
FIGS. 17 and 18 illustrates an aortocaval shunt rivet formed with a single wired wrapped to form the device.
Figure 18:
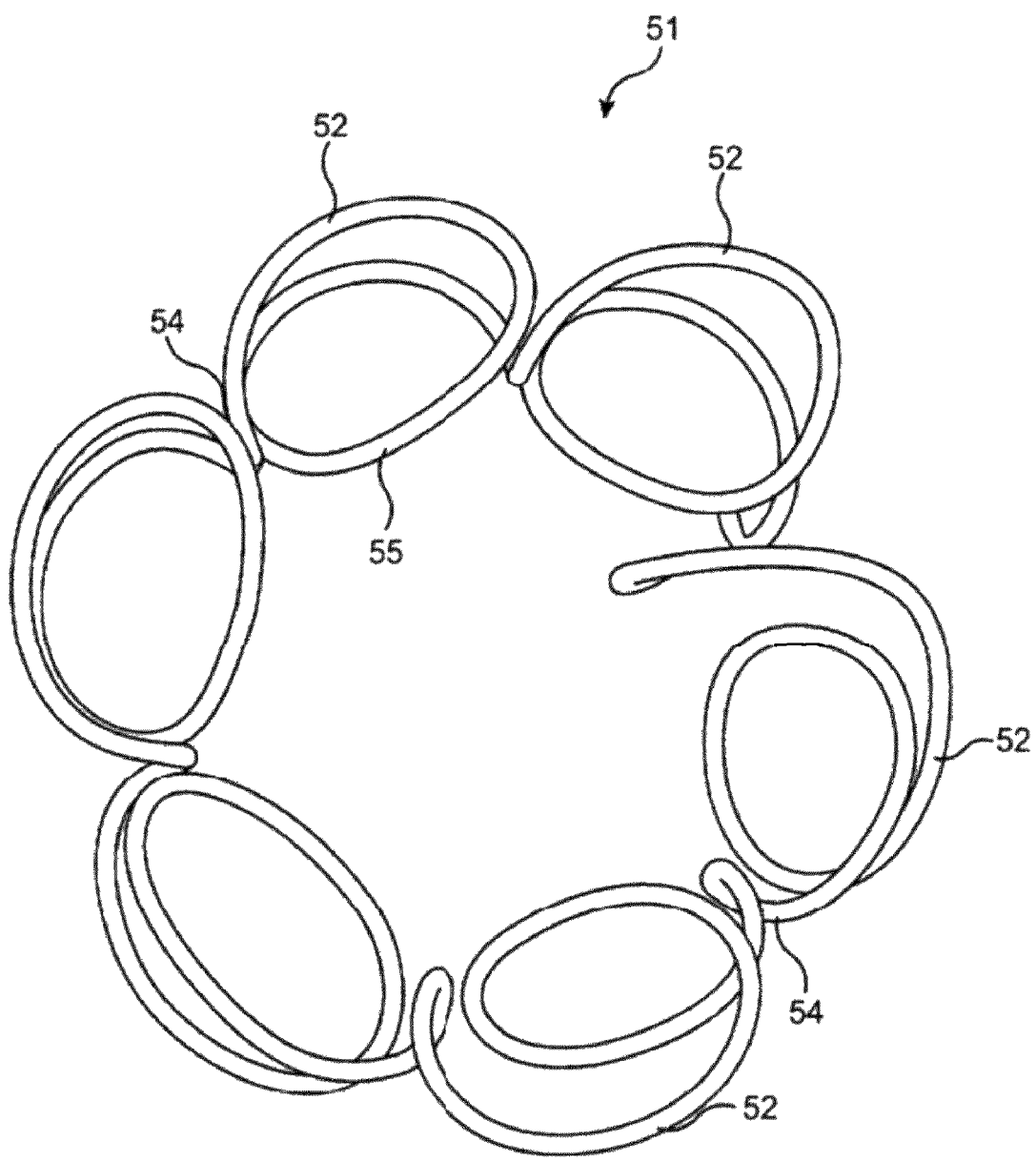

FIGS. 17 and 18 illustrate an aortocaval shunt rivet 51 formed with a single wired wrapped to form the device. In this device, a single wire has been wrapped around a specially formed mandrel to form a number of clinch members 52 on one end of the device and a number of clinch members 53 on the other end of the device. As illustrated, each clinch member is slanted relative to the radius of the device, and the wires forming the waist segment of the device are also oblique to the longitude of the device. As viewed from the top, each clinch member comprises a substantially circular arc, and the wire continues from the arc longitudinally toward the opposite end of the device, forming straight waist segment 54 where it runs substantially parallel to the long axis of the device until it arcs circumferentially away from the previous arc to form the clinch member on the opposite end, whereafter it loops around to extend retrograde relative to the circumference, forming waist segment 55 running obliquely relative to the long axis, and back toward the first end of the device until it curves again circumferentially forward to form the loop of the next clinch member circumferentially adjacent the first loop and longitudinally in line with the immediate previously formed clinch member on the opposite end of the shunt rivet, and continues in this fashion until the entire tubular structure of the device is achieved. In tracing its path, the wire may cross over one or more other portions of the wire.

Figure 19:
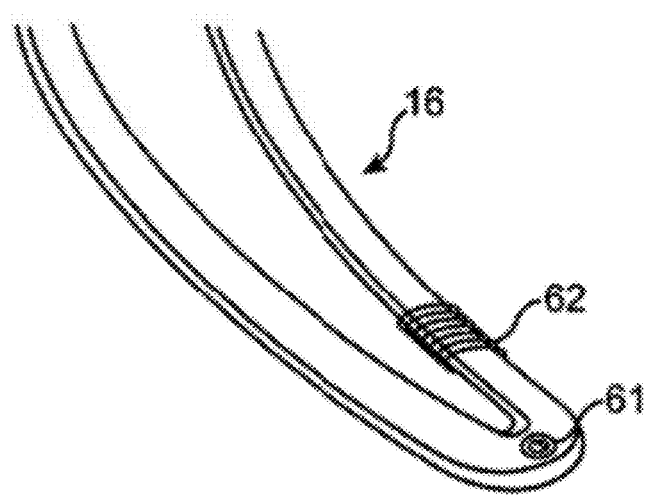
FIG. 19 shows a detail of the clinch member, illustrating radiopaque markers on the shunt rivet.

FIG. 19 shows a detail of the clinch member, illustrating radiopaque markers on the shunt rivet. A radiopaque marker may be provided in the form of a radiopaque rivet 61 disposed near the tip of the clinch member 16, or it may be provided in the form of a wrapped coil of radiopaque wire or thread 62. The radiopaque markers may be comprised of platinum, iridium, tantalum, barium sulfate or other radiopaque materials. Similar markers may also be applied to the waist section. The marker material may also be selected to enhance visibility under ultrasound imaging, magnetic resonance imaging, or other suitable imaging techniques.

Figure 21:
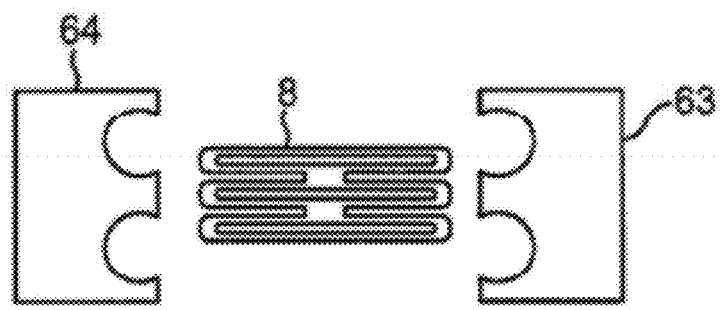
FIGS. 20 and 21 illustrate a mandrel useful for forming and training/heat setting the shunt rivets.
Figure 20:
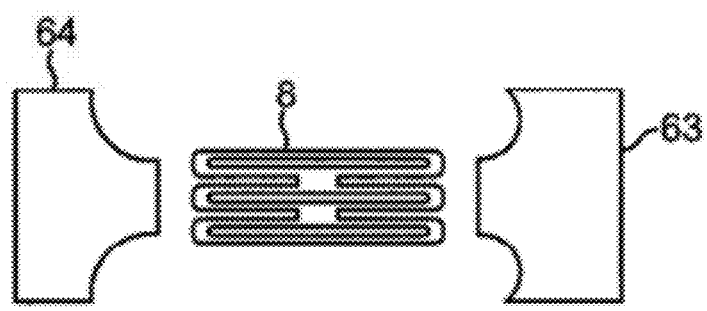

FIGS. 20 and 21 illustrate mandrels or dies useful for forming and training/heat setting the shunt rivets. As shown in FIG. 20, a two-part mandrel comprises a distal mandrel portion 63 and a proximal mandrel portion 64. Each mandrel is shaped to correspond to the desired final shape of the shunt rivet and its clinch members. The mandrel portions are inserted into the tube, after it has been cut, so as to deform the device. Where the device is formed from a pseudoelastic material that must be heat set or trained, the mandrels are dimensioned to deform the device to its desired open configuration. Where the device is formed of spring steel or the like, the mandrel is dimensioned to bend the clinch members beyond the desired final configuration. Thus, the mandrel of FIG. 20 and the mandrel of FIG. 21, though shaped differently, may be used to form quite similar shapes for devices made of nitinol and spring steel. The mandrel shapes may be modified as desired to achieve various clinch member shapes, such as the asymmetrical shapes shown in FIGS. 12 and 13.

Figure 22:
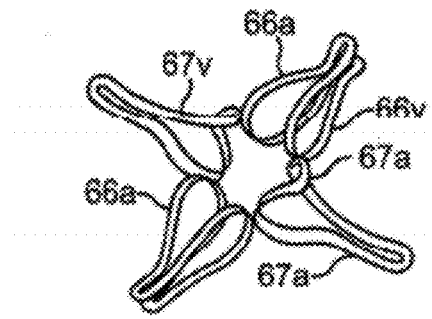
FIG. 22 is a perspective view of a shunt rivet in which the clinch members are biased to provide a pair of clinch members biased to close upon contiguous parallel portions of adjacent vessels while exerting slight pressure on circumferentially spaced points on the side walls of the adjacent blood vessels.

The shunt rivet may be modified as shown in FIGS. 22 through 25. FIG. 22 is a perspective view of a shunt rivet 65 in which the clinch members are biased to provide pairs of clinch members 66*a* and 66*v* biased to close upon contiguous parallel portions of adjacent vessels and a pair of clinch members 67*a* and 67*v* biased to exert slight pressure, and establish slight compliance mismatch, on circumferentially spaced points on the side walls of the adjacent blood vessels. Each clinch member is slit down the center to allow radially expansion of the device through radial deformation of the clinch member.

Figure 23:
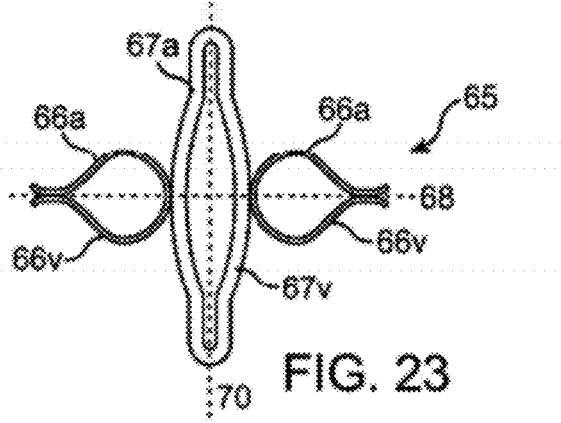
FIG. 23 is a side view of the shunt rivet 22 showing the substantial closure of longitudinally oriented clinch members.
Figure 24:
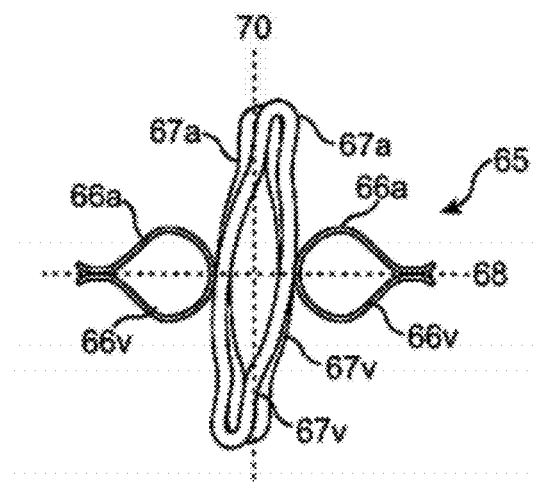
FIG. 24 is a side view of the shunt rivet 22 showing the preferred angle of the transversely oriented clinch members relative to the axis of the device.

FIG. 23 is a side view of a shunt rivet of FIG. 22 showing the substantial closure of longitudinally oriented clinch members 66*a* and 66*v*. These clinch members are formed to evert, such that the tips of opposing clinch members 66*a* and 66*v* are closely proximate each other when released (in the expanded configuration shown). A short segment at the distal tip of each clinch member is turned away from the transverse midline 68 of the device to form an atraumatic bearing surface for impingement on the blood vessels walls. As illustrated, the clinch members 66a and 66v comprise a continuously formed clip, with no intervening waist segment between the arterial portion of the clip and the venous portion of the clip. The clip resembles a tool clip, as that term is used in other arts. Preferably the clinch members making up the tool clip are joined directly together, without an intervening rectilinear base (though a rectilinear base may be incorporated if desired to accommodate the anatomy of the arterio-venous fistula in a particular site), to create a smoothly arcuate transition from the distal clinch member to the proximal clinch member. FIG. 24 is a side view of the shunt rivet 22 showing the preferred angle of the transversely oriented clinch members 67a and 67v relative to the axis 70 of the device. In this embodiment, the transversely oriented clinch members 67a and 67v (both the near and far pairs are visible in this view) are set at a small angle from axis 70. In the unrestrained configuration, the clinch members 67a on the arterial side of the device (typically the first side of the device to be released from the catheter given the preference for transvenous delivery) are inclined toward the upstream or retrograde direction. Clinch members 67v on the venous side of the device are inclined toward the upstream or retrograde direction within the vein. This configuration facilitates release of the device from the small delivery catheter used to insert it into a fistula.

Figure 25:
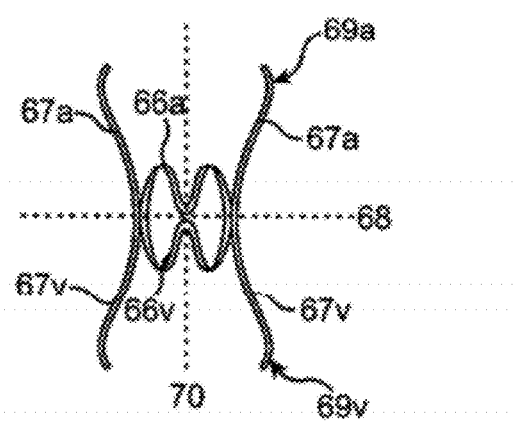
FIG. 25 is a side view of the shunt rivet of FIG. 22 showing transversely oriented clinches.

FIG. 25 is a side view of the shunt rivet of FIGS. 22 through 24 showing transversely oriented clinch members 67a and 67v with substantial spacing between the tips of the clinch members (in the expanded configuration shown). Also, clinch members 67a and 67v constitute a continuously formed tension spring (shaped substantially like the tension spring used in window frames, having an arcuate or bow shape, with the ends arcing outwardly from the axial centerline 70 of the device and adapted to impinge upon or exert force on the blood vessels and the middle of the arch adapted to exert force on the remainder of the shunt rivet to which it is fixed), with no intervening waist segment between the arterial portion of the tension spring and the venous portion of the tension spring, and the tension spring formed to impinge on the sidewall of the artery or vein at a point circumferentially displaced from the center of the rivet without deforming the artery and/or vein walls to bring the opposite tips 69a and 69v into apposition such as that achieved by the tips of the tool clips. A short segment at the distal tip of each clinch member is turned away from the axial centerline 70 of the device to form an atraumatic bearing surface for impingement on the blood vessel walls.

The device may thus be described, in their open and unconstrained conditions, as comprising two parallel tool clips secured at their closed ends to two parallel tension springs, at the midpoints of the tension springs, to create an orthogonal or cruciform grouping of alternating spring clips and tension springs. Adopting the botanical language used for other embodiments, each side of the device comprises a pair of petaloids arcing outwardly from the axial centerline of the device without everting (without a substantial arc in the proximal direction), and a pair of petaloids arcing outwardly and everting with a substantial arc in the distal direction, with corresponding petaloid structures being joined at their proximal ends without an intervening waist segment. Each petaloid is formed in an open frame V-shape. Though illustrated with a pair of clips and a pair of tension springs, the device may be formed with additional tension springs or clips, as dictated by the local anatomy of a particular installation. In appropriate anatomical conditions, the device may comprise four clips in the tool clip configuration, or the comparable everting petaloid pairs (in which all clinch members evert substantially to close upon the vessel wall), arranged orthogonally, where the tool clips are arranged in a circular arrangement with the closed end of each clip being secured to the closed and of an adjacent clip, such that the open end of each tool clip is directed outwardly from the circular arrangement. The device may also include additional arcuate tension springs and/or tool clip portions, thus departing from the cruciform configuration shown while achieving the benefit of substantial spacing of the vessel contacting tips from the arterio-venous fistula.

Figure 26:
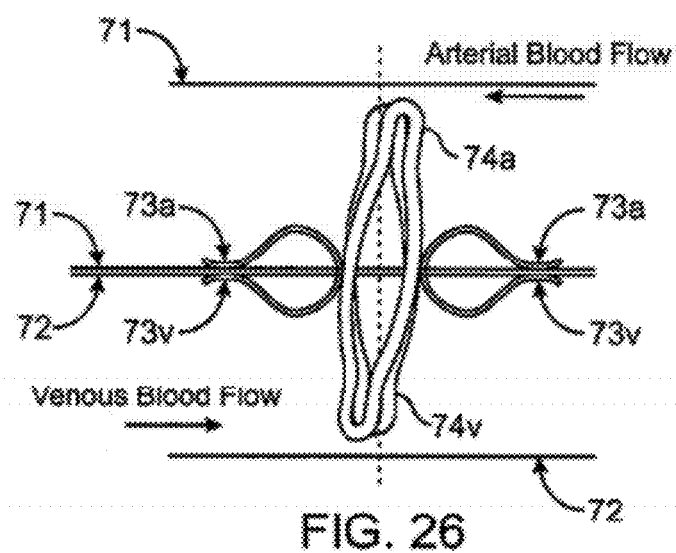
FIG. 26 shows the shunt rivet of FIGS. 22 through 25 installed between an artery and a vein, illustrating the construction of the device relative to the environment of use.

FIG. 26 shows the shunt rivet of FIGS. 22 through 25 installed between an artery 71 and vein 72, in order to illustrate the construction of the device relative to the environment of use. The tips of the "tool clip" portion of the device (66a and 66b) close upon points in the respective vessels 73a and 73v which are longitudinally spaced (relative to the blood vessels) from the arterio-venous fistula formed in which the device is placed. The points of impingement are significantly spaced from the fistula, as illustrated. The tips of the tension spring portion (67a and 67v) of the device impinge on circumferentially spaced points 74a and 74v. As shown in FIG. 26, the circumferential points of impingement are significantly spaced from the fistula. The circumferential spacing is preferably 30° to 90°, but may be adjusted to fit local anatomy. In this manner, the shunt rivet avoids engagement of the blood vessels adjacent the fistula. As shown in FIG. 26, the ultimate shape of the installed shunt rivet may vary from the unrestrained shape due to the remaining constraint of the blood vessel walls, though the device is biased to resiliently or superelastically return to the unrestrained shapes of FIGS. 22 through 25. After installation, the shunt rivet holds the adjacent artery and vein together and maintains an open flow path through opening defined by the roughly circular arrangement of the clips and tension springs. Should the arrangement appear to be somewhat squared or angular, pentagonal, hexagonal, etc., given the particular geometries of the various parts, it is intended that such departures from perfect circular arrangement be included under the description of a circular arrangement.

Figure 27:
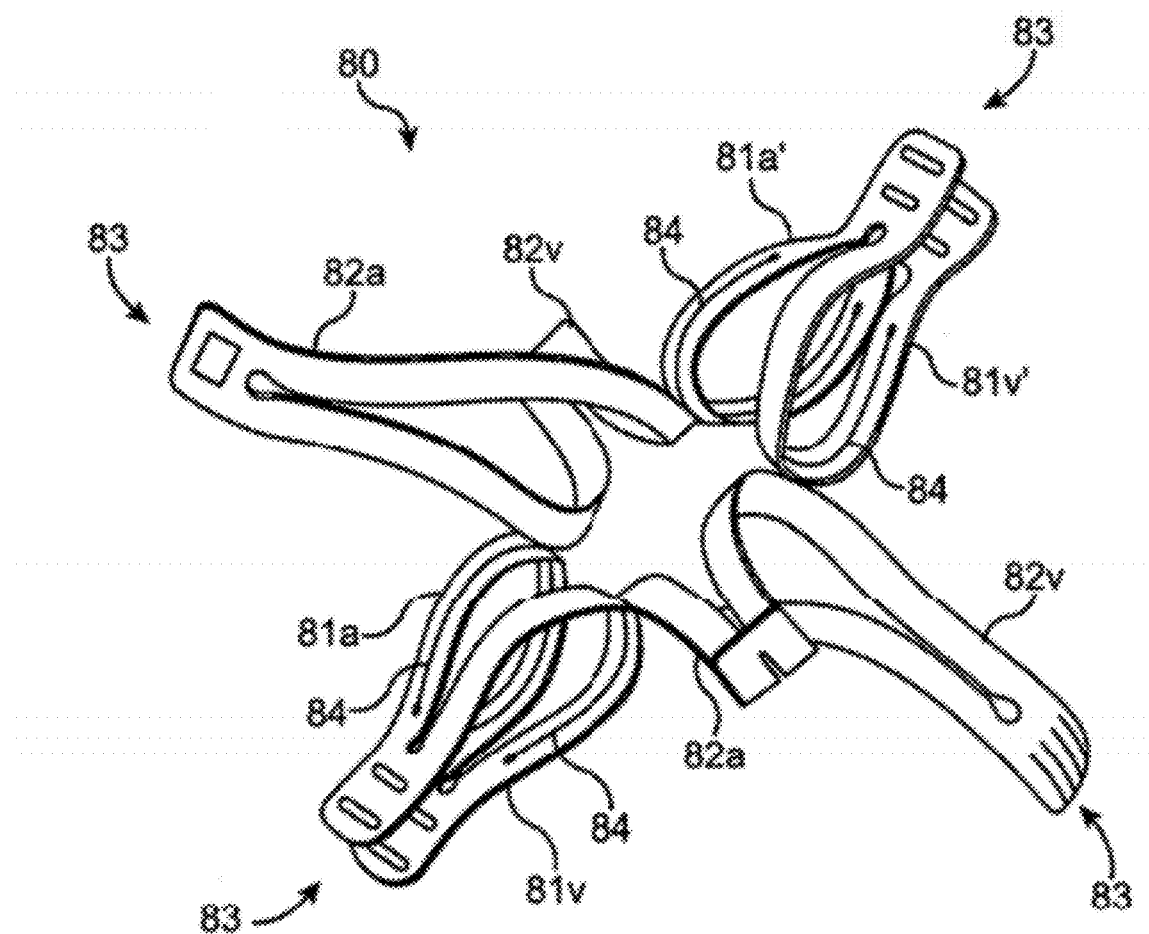
FIG. 27 shows another variation of shunt rivet which may include varying lengths of the respective clinch members.

Yet another variation for the shunt rivet may include varying a length of the respective clinch members. As illustrated in the perspective view of FIG. 27, shunt rivet 80 may include the longitudinally oriented clinch members 81a, 81a' and 81v, 81v' positioned opposite to one another and transversely oriented clinch members 82a and 82v positioned transverse relative to an axial centerline of shunt rivet 80, as described above. In this variation, clinch members 81a and 81v' may be sized to have a length which is less than clinch members 81a' and 81v, as described in further detail below. The respective lengths of clinch members 81a, 81v' relative to 81a', 81v may be variably sized to maximize or optimize the stability of shunt rivet 80 with respect to the vessels when deployed between adjacent vessels.

Moreover, varying the lengths of the respective clinch members may further provide additional advantages. For instance, the clinch members which are shortened in length may facilitate the positioning and securement of the shunt rivet between the vessels by allowing for the relatively shorter member to swing into position within the vessel lumen during deployment, as described in further detail below. Moreover, a shorter member may provide for a minimized implant size when placed against the vessel interior wall for securement as well as a mitigating any physiologic reaction to the implant, e.g., a reduction in thrombosis, etc. Additionally, clinch members which are lengthened relative to other members may provide for increased shunt stability by increase the amount of force applied against the tissue walls.

Moreover, clinch members having different lengths may additionally place the adjacent vessels in tension such that the vessel walls are drawn towards one another and the clinch members 81*a*, 81*a'* and 81*v*, 81*v'* contact the vessel luminal walls to stabilize not only the shunt rivet within the vessels but also the vessels with respect to one another. Additionally, having one or more clinch members 81*a*, 81*v'* sized to have a length shorter than its respective apposed clinch member may also facilitate the deployment and/or positioning of the clinch members 81*a*, 81*v'* within the vessel since the shorter length clinch members can more easily "swing" through an arc within the vessel lumen without contacting the interior walls. Clinch members with differing lengths may further be configured to align along different planes when deployed to facilitate vessel separation, if so desired.

As above, each of the clinch members may be formed without an intervening waist segment between the arterial portion of the shunt rivet 81*a*, 81*a'* and the venous portion of the shunt rivet 81*v*, 81*v'*. As also previously described, the clinch members may be joined directly together, without an intervening rectilinear base (though a rectilinear base may be incorporated if desired to accommodate the anatomy of the arterio-venous fistula in a particular site), to create a smoothly arcuate transition from the distal clinch member to the proximal clinch member.

Aside from the variable length clinch members, shunt rivet 80 may further define one or more slots 83 along the length of the clinch members, such as at the terminal ends of each clinch member. The one or more slots 83 may be formed or cut, e.g., by a laser, to provide a region through which a radio-opaque marker or wire, such as tantalum wire or any other radio-opaque material as described herein, may be passed through to facilitate imaging during deployment. Shunt rivet 80 may also further include an optional radio-opaque center marking band about the center of rivet 80 to indicate the center, e.g., when viewed under fluoroscopy or any other imaging modality. Additionally, one or more of each clinch member may also optionally include a slot 84 defined along a length of the individual respective clinch member struts, as shown, to further function as a stress-relieving slot.

Figure 28:
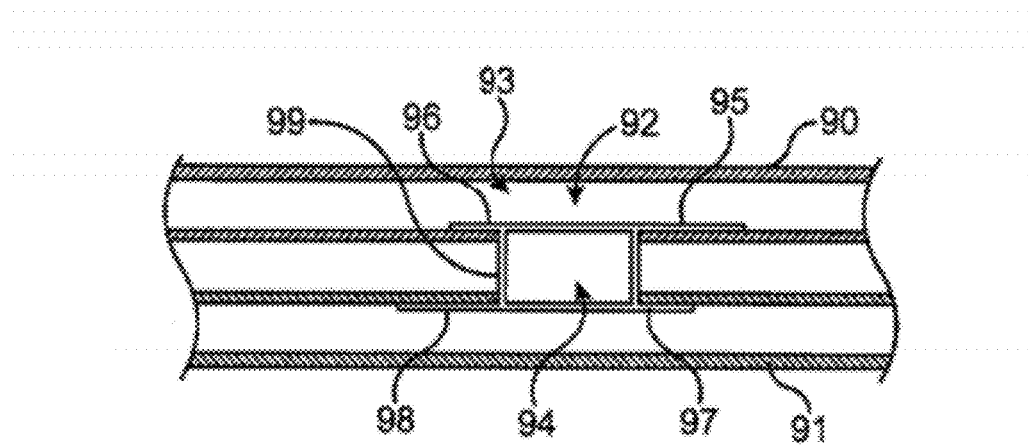
FIG. 28 shows a partial cross-sectional view of another variation of a shunt rivet as deployed having clinch members of differing lengths.

Although shunt rivet may be formed without an intervening waist member, it may be optionally included. As shown in the illustrative partial cross-sectional view of FIG. 28, another variation of shunt rivet 93 may be seen deployed between two respective vessels, artery 90 and vein 91. Clip connector 99 may extend between sets of clinch members 95, 96 and 97, 98 while defining lumen 94. Although the transverse clinch members have been omitted from the illustration for clarity, they may be optionally omitted from the shunt rivet entirely, if so desired. In its deployed configuration when placed through fistula 92 defined between vessels 90, 91, lumen 94 may define a flow path between the vessels, as described above. In this variation, clinch members 96, 97 are shortened in length relative to the lengths of clinch members 95, 98. The shortened clinch members 96, 97 may be configured to be deployed on opposite ends of the shunt rivet such that shortened clinch member 96 is disposed within artery 90 while shortened clinch member 97 is disposed within vein 91 and extends in a direction opposite to that of clinch member 96. Shortened clinch members 96, 97 may be similar in length and configuration or they may be varied in length relative to one another.

Likewise, clinch member 95 may be disposed in artery 90 while clinch member 98 is disposed in vein 91 such that they extend in opposing directions and are positioned opposite to their respective shortened clinch members. Like their shortened counterpart members, clinch members 95, 98 may be similar in length and configuration or they may also be varied in length relative to one another. Clinch members with differing lengths may be utilized in any of the variations described herein in combination with additional features, as described.

Figure 29:
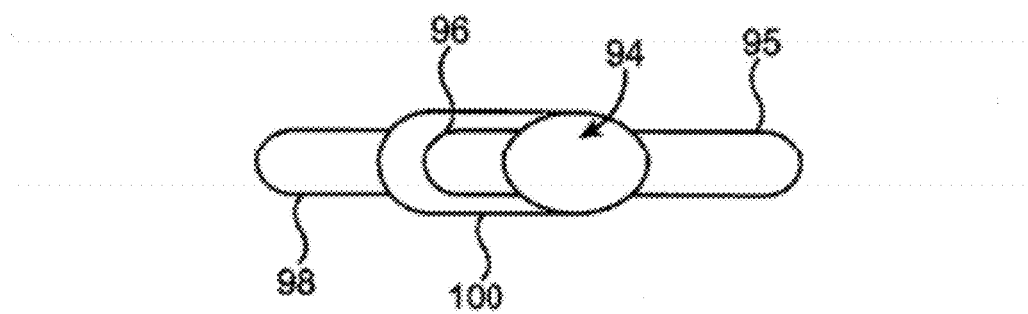
FIG. 29 shows a top view of another variation of a shunt rivet having an angled connector between the clinch members, which may also have differing lengths.

In addition to having clinch members of different lengths, the connector member itself may be modified such that its extends between the respective clinch members at an angle relative to a centerline of the shunt rivet, as illustrated by angled connector 100 in the top view of FIG. 29. The angled connector 100 may be configured over a number of various angles such that the blood flow between the vessels 90, 91 through angled connector 100 avoids a 90° turn.

Figure 30:
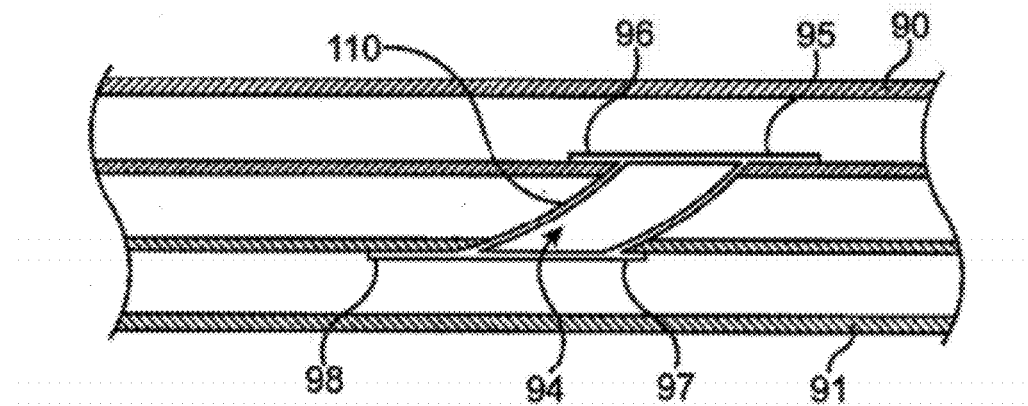
FIG. 30 shows a partial cross-sectional view of yet another variation of a shunt rivet having an angled connector which may also be tapered along its length.

In yet another variation, angled connector 110 may be further modified such that the cross-section of the connector is tapered along its length, as shown in the partial cross-sectional view of FIG. 30. Accordingly, in addition to having clinch members of various lengths and an angled connector, the connector 110 and/or connector lumen 94 may be tapered or it may define a non-constant cross-sectional area along its length. For instance, the connector lumen 94 may be tapered such that the cross-sectional area increases as the connector 110 extends from the arterial vessel 90 to the venous vessel 91, as shown. Alternatively, the cross-sectional area may decrease as the connector 110 extends away from the arterial vessel 90.

Figure 31:
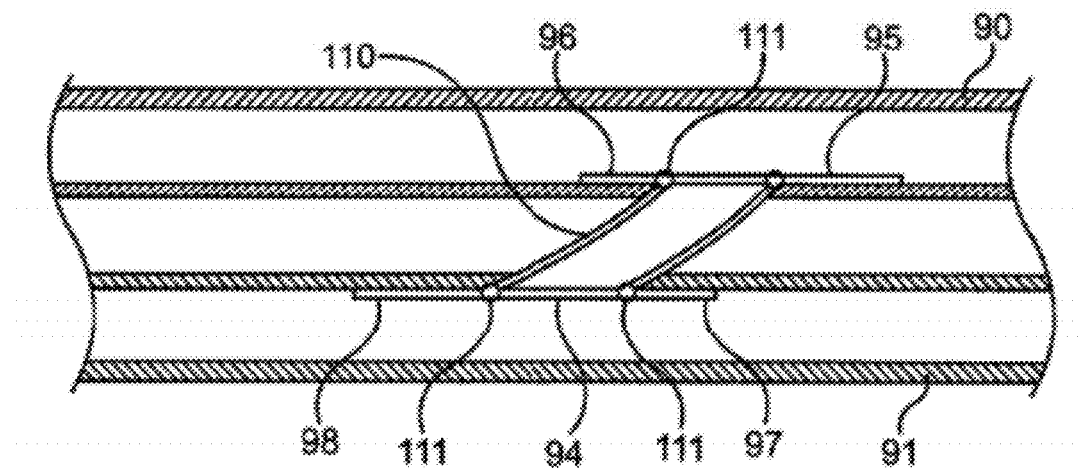
FIG. 31 shows a partial cross-sectional view of yet another variation of a shunt rivet having hinges or flanges between the clinch members and the connector to adjust or change an angle between the shunt rivet and the vessels.

In yet a further variation, the shunt rivet may optionally include a hinge or flange 111 connecting one or more of the clinch members to the connector 110, as shown in FIG. 31. Such a hinge or flange may be adjustable to change an angle at which connector 110 extends between the clinch members and may utilize any number of hinging mechanisms. For instance, hinge or flange 111 may simply comprise a plastically deformable portion of the shunt rivet or it may be a mechanically hinged mechanism, e.g., which provides for frictional engagement between the clinch members and the connector 110 to maintain its position yet also allows for adjustment. The hinge or flange 111 may be adjusted prior to deploying the shunt rivet such that the clinch members extend at their predetermined angle when deployed. Alternatively, hinge or flange 111 may be adjusted during deployment or after the shunt rivet has been placed between the vessels 90, 91 by using an inflatable balloon instrument or other expandable tool. In yet another alternative, the hinge or flange 111 may be adjusted both before deployment and during or post deployment into the vessels. For example, post deployment adjustments may be accomplished anytime, e.g., within one hour of shunt deployment, or alternatively in a subsequent procedure, e.g., prior to or after thirty days of deployment within a patient.

Figure 32:
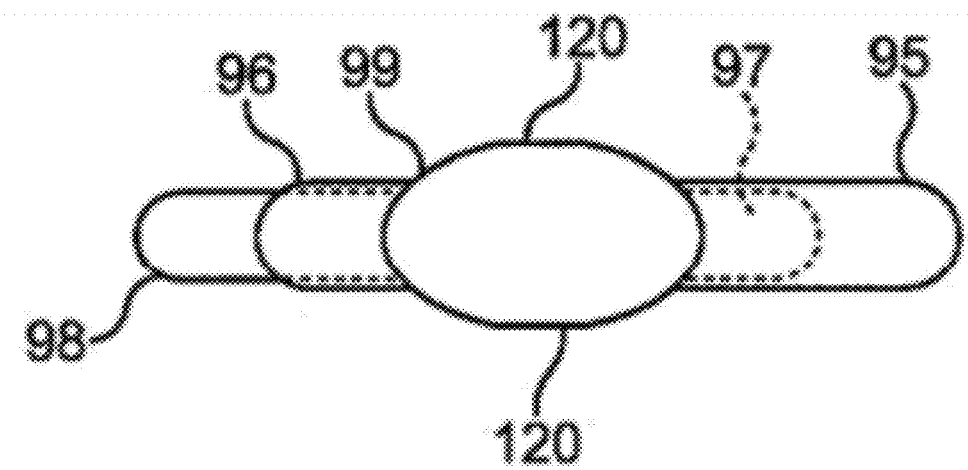
FIG. 32 shows a top view of another variation of a shunt rivet having one or more break-away or frangible segments which may be integrated with the shunt rivet along a periphery of the connector.

Another variation may utilize one or more break-away or frangible segments 120 which may be integrated with the shunt rivet along a periphery of connector 99, as illustrated in the top view of FIG. 32. In this example, two break-away segments 120 may be integrated on either side of connector 99 such that when the shunt rivet has been positioned or during positioning into the vessels, connector 99 may be adjusted in size, e.g., by expanding the opening via a balloon instrument, to allow for a greater flow through the shunt rivet. The break-away segments 120 may be comprised of a number of different biocompatible materials which may be dissolved into the blood or they may be configured as opposing portions of connector 99 which are overlapped or otherwise held temporarily to one another.

Alternatively, segments 120 may be comprised of plastically deformable bands which break apart to adjust or allow for the adjustment of the cross-sectional area of the connector 99. The adjustability of the connector cross-section may allow for the shunt rivet to change from a circular cross-sectional area to an oval cross-sectional area. In the same manner, the cross-sectional area may be changed from an oval area to a round area. The adjustment of the cross-sectional area utilizing the break-away segments 120 may be performed pre-implantation, during implantation, or post implantation of the shunt rivet into the vessels.

Figure 33:
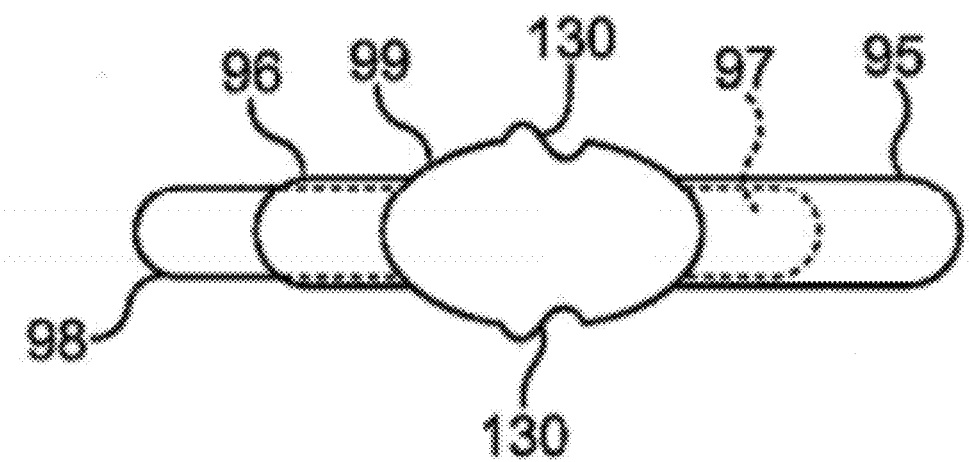
FIG. 33 shows a top view of another variation of a shunt rivet having one or more plastically deformable sections which may be integrated along the periphery of the connector.

Another variation is shown in the top view of a shunt rivet in FIG. 33 which utilizes one or more plastically deformable sections 130 which may be integrated along the periphery of connector 99. As shown, the plastically deformable sections 130 may be plastically deformed, e.g., via an inflatable balloon, either prior to, during, or post deployment to adjust the cross-sectional area of connector 99. Moreover, plastically deformable sections 130 may be integrated into connector 99 such that when connector 99 is expanded or deformed, sections 130 plastically deform and retain their deformed configuration when a deforming force is removed.

Figure 34:
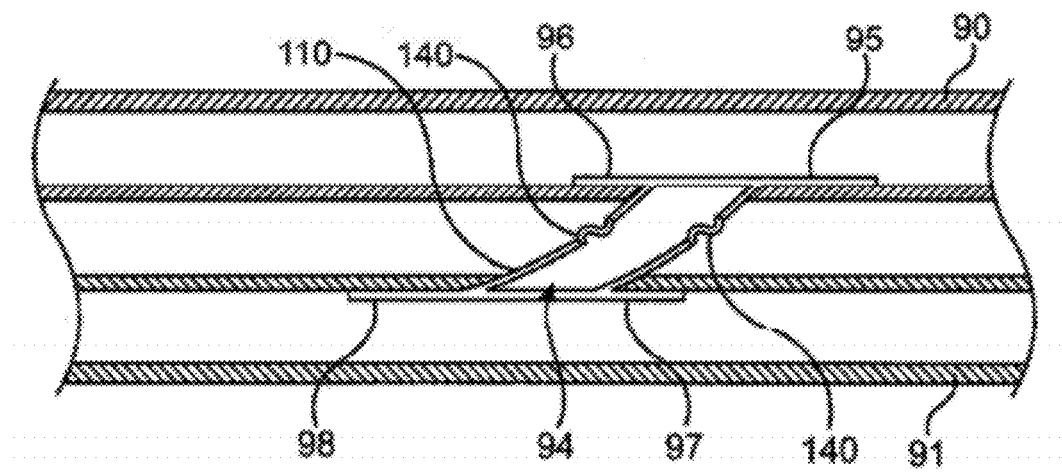
FIG. 34 shows a partial cross-sectional view of yet another variation of a shunt rivet having plastically deformable, elastically deformable, or break-away segments or portions along a length of the connector to adjust a length of the lumen through which blood is shunted.

Aside from variations in adjusting the cross-sectional flow area of the shunt rivets, other optional variations may be incorporated in any of the shunt rivets described herein. For instance, FIG. 34 shows a partial cross-sectional side view of yet another variation which may utilize plastically deformable, elastically deformable, or break-away segments or portions 140 along a length of connector 110 to adjust a length of the lumen through which blood is shunted. The portions 140 may be utilized along a length of connector 110 to allow for adjustment of the distance between the vessels 90, 91 and they may be utilized with a connector length which is uniform in diameter or which is tapered or narrowed, as described above.

Figure 35A:
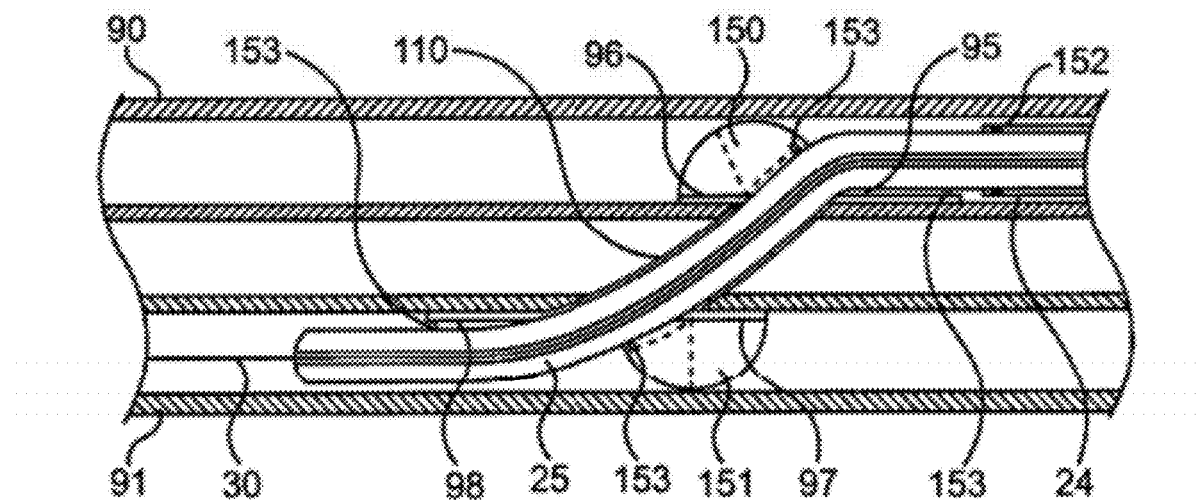
FIG. 35A shows a partial cross-sectional view of yet another variation of a shunt rivet illustrating an example of an ordered sequence in which the clinch members may be deployed.

In utilizing a shunt rivet having different clinch member lengths, shorter length clinch members can more easily "swing" through an arc within the vessel lumen without contacting the interior walls, as mentioned above. Accordingly, such a shunt rivet may be implanted such that the clinch members are deployed in an ordered sequence. In one example, once a needle has been passed through the tissue wall to cross between vessels 90, 91, guidewire 30 may be advanced intravascularly through the needle which may then be removed leaving guidewire 30 passing through vessels 90, 91. Shaft 25 and/or outer sheath 24 may be advanced through vessel 90 over or along guidewire 30 to follow guidewire 30 into vessel 91, as shown in FIG. 35A. Shaft 25, described above, may be fabricated with a stiffened tip, such as polyimide, to facilitate crossing between vessels. Once properly positioned within vessel 91, outer sheath 24 may be pulled proximally while tracking its distal end visually via a marker band 152 until clinch member 98 is first released from the constraints of outer sheath 24 and allowed to reconfigure itself into its angled configuration, relative to a longitudinal axis of the shunt rivet. The individual clinch members of the shunt rivet may be optionally retained via anchoring pins 153 integrated with shaft 25 which may hold the clinch members in place as outer sheath 24 is retracted. These anchoring pins 153 may also serve to prevent or limit the motion of the shunt rivet itself until outer sheath 24 has been fully retracted. This particular configuration may be utilized in situations where a clinician may wish to re-sheath the shunt rivet, e.g., for abandoning a procedure or for repositioning the shunt rivet, etc.

With outer sheath 24 pulled further proximally, shortened clinch member 97 may be subsequently released. With its shortened length, relative to clinch member 98, clinch member 97 may fully deploy and arc 151 entirely within vessel 91 without interfering or contacting the distal region of the vessel wall until clinch member 97 comes into contact against the proximal region of the vessel wall. With clinch members 97, 98 fully deployed within vessel 91, outer sheath 24 may be further withdrawn relative to shaft 25 to subsequently release shortened clinch member 96, which may then arc 150 entirely within adjacent vessel 90 to contact the tissue surrounding the fistula. Subsequently, outer sheath 24 may be fully retracted to release clinch member 95 to allow it to come into contact against the tissue wall within vessel 90, thereby fully deploying the shunt rivet between vessels 90, 91. The shunt rivet may be partially deployed from shaft 25 and optionally removed and/or re-positioned and re-deployed elsewhere within the body.

Figure 35B:
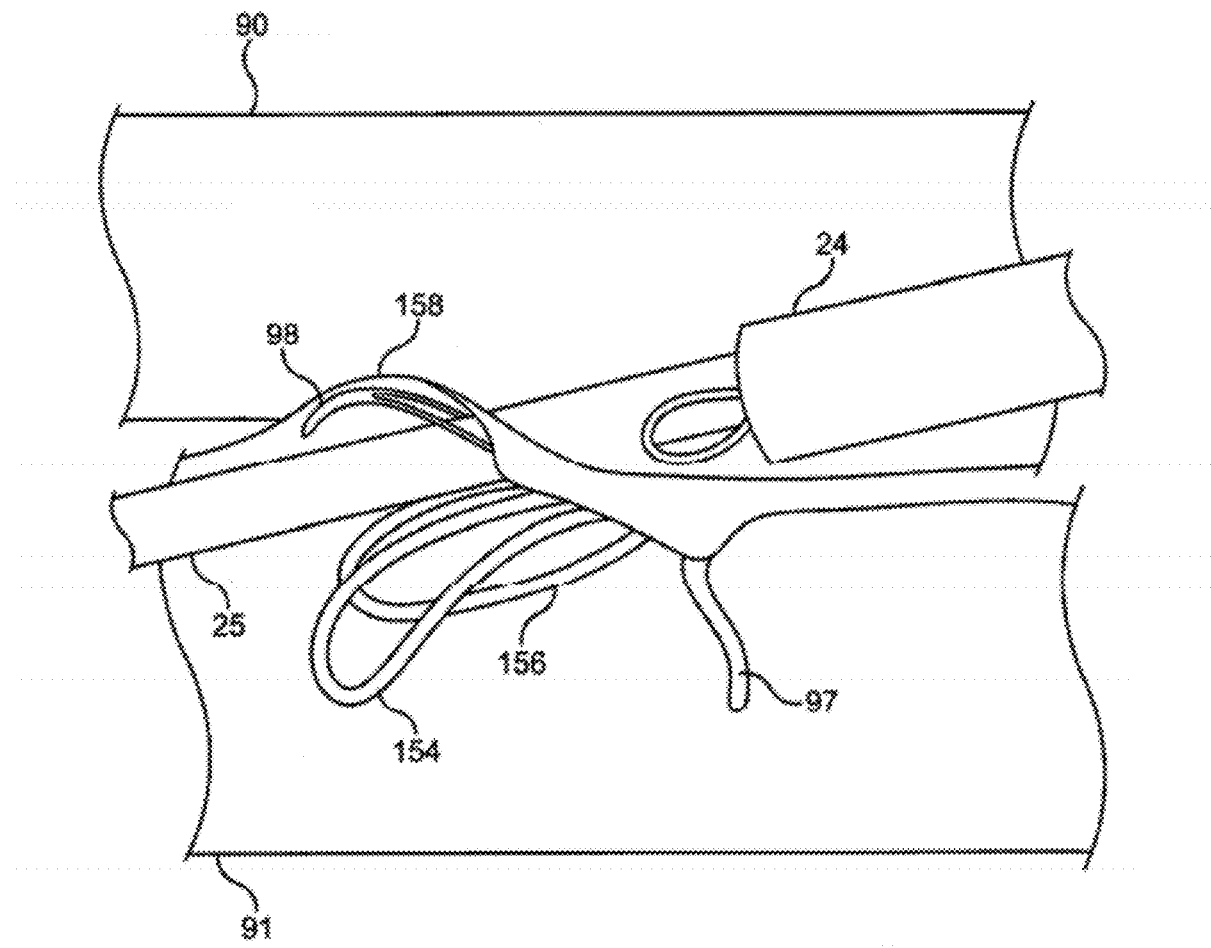
FIGS. 35B and 35C illustrate side views, respectively, of clinch members of a shunt rivet being deployed entirely within a vessel.
Figure 35C:
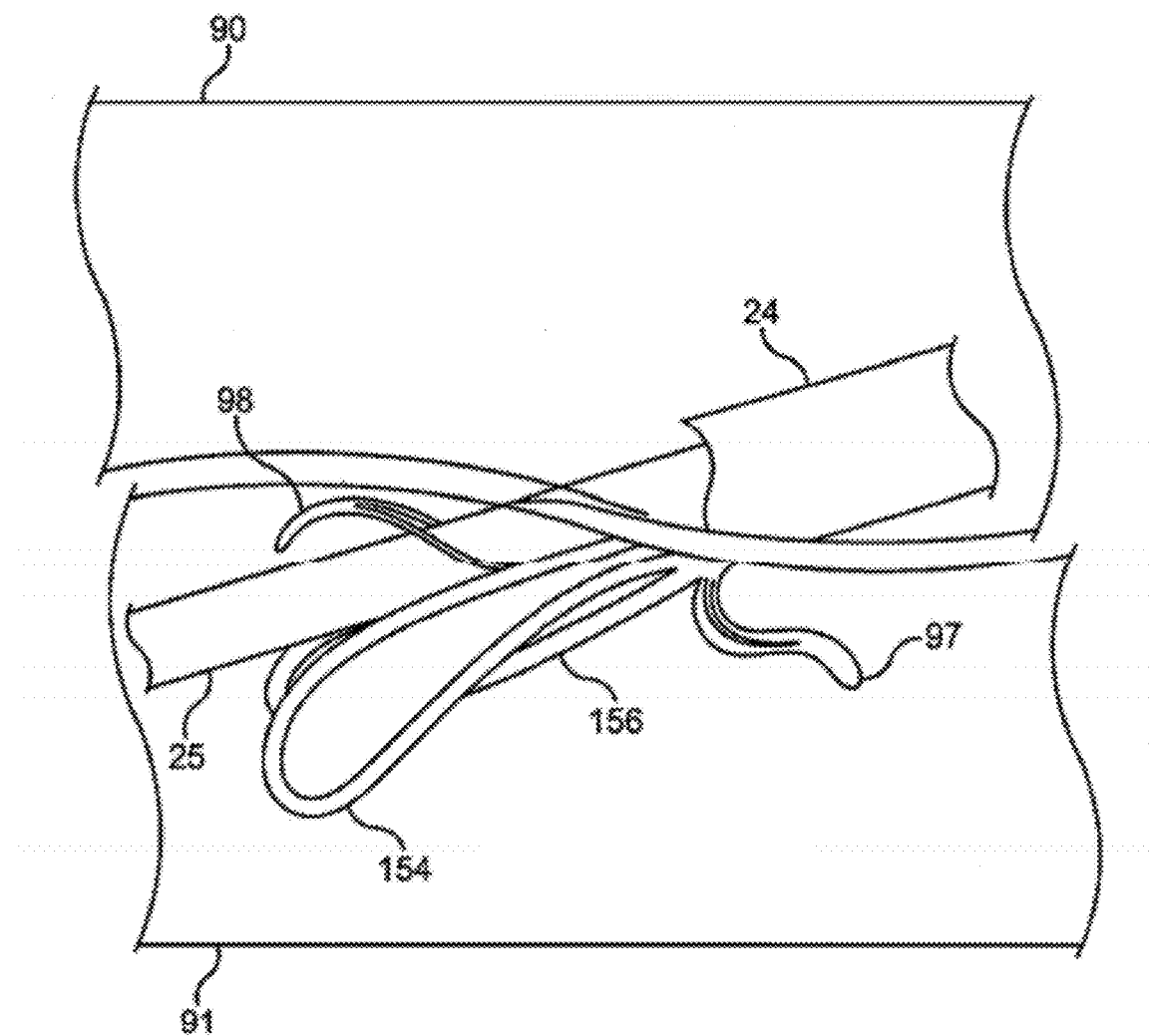

Another example is illustrated in FIGS. 35B and 35C, which illustrate side views of clinch members of a shunt rivet being deployed entirely within a vessel. As shown in FIG. 35B, once the assembly has been advanced intravascularly through vessel 90, e.g., an artery, and the needle and guidewire advanced from within vessel 90 and into adjacent vessel 91, e.g., a vein, shaft 25 carrying the shunt rivet may be advanced at least partially from outer sheath 24 (alternatively, outer sheath 24 may be retracted relative to shaft 25) to expose the transversely oriented clinch members 154, 156 and the clinch members 97, 98 for expansion and/or reconfiguration within vessel 91. As shown, clinch member 97 may reconfigure from a low profile configuration where clinch member 97 is positioned to extend distally along shaft 25 during delivery to a configuration where member 97 swings proximally within vessel 91, as shown, to a securement configuration.

One or more members can be deployed and by advancing the outer sheath 24 (and/or retracting shaft 25 relative to outer sheath 24), the members can be recaptured and at least partially re-sheathed to allow for removal and/or repositioning of the shunt rivet. Once desirably repositioned, the clinch members may be fully deployed into position.

As further illustrated in this example, the lengthened clinch member 98 may engage against the vessel wall within vessel 91 during deployment. If excessive pull force is applied to the shunt rivet, member 98 can deform and straighten while deflected by the walls of vessel 91, as illustrated by deformed tissue 158, so as to prevent or inhibit damage to the surrounding tissue. A clinician can visually assess, e.g., via fluoroscopy or ultrasound, the wall-to-shunt engagement by gauging the amount of deflection indicated by the lengthened clinch member 98. Along with the tactile feedback perceived by the clinician, the visual indication of the clinch member deformation may further aid in confirming suitable shunt rivet positioning.

Once the position of the shunt rivet has been confirmed within vessel 91, clinch member 98 may be fully deployed and clinch member 97 may be fully deployed to swing proximally into its securement position within vessel 91, as shown in FIG. 35C. The remaining clinch members may be subsequently released from outer sheath 24 and shaft 25 to be deployed within vessel 90.

In delivering and configuring the shunt rivets described above, additional delivery instruments may be utilized to facilitate adjustment of the shunt rivets to a desirable configuration. For instance, adjusting the cross-sectional area of the connector portion of the shunt rivet or adjusting a length of the connector lumen between the clinch members, or adjusting an angle of the shunt rivet and clinch members with respect to the vessel lumens, etc., may be accomplished with instruments as shown in FIGS. 36 to 38.

Figure 36:
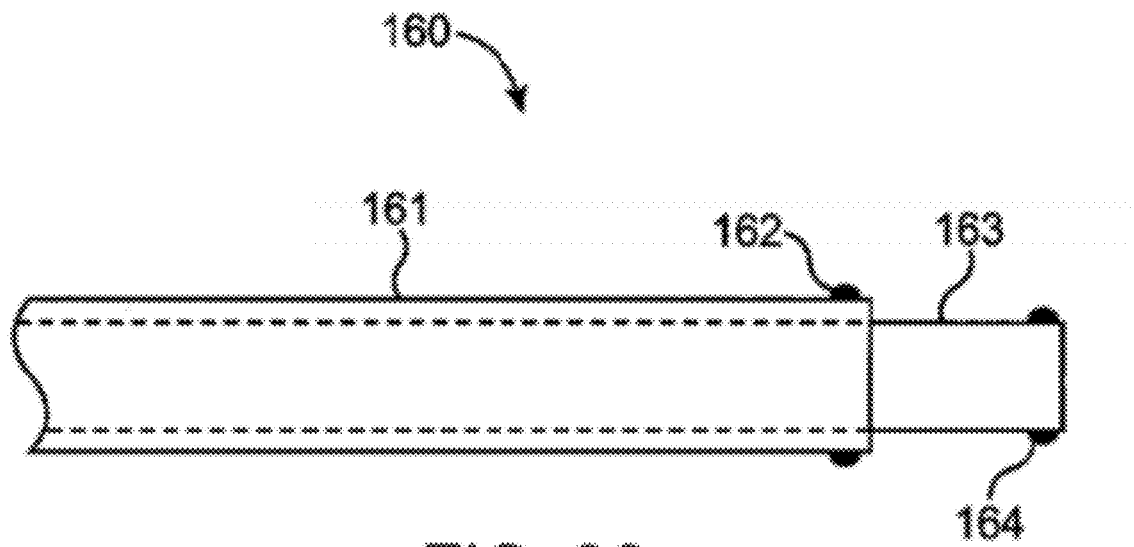
FIG. 36 shows a side view of one variation of an instrument which may be used to adjust a length of the connector lumen.

FIG. 36 illustrates one variation of an instrument 160 which may be used to adjust a length of the connector lumen. Instrument 160 may generally comprise an outer sheath 161 having an inflatable balloon or expandable member 162 disposed around a distal portion of the sheath 161. Inner sliding core 163, upon which the shunt rivet may be disposed upon or over, may be slidingly disposed within outer sheath 161 and may also have an inflatable balloon or expandable member 164 also disposed around a distal portion of core 163. As mentioned above, with the shunt rivet disposed upon sliding core 163, inflatable members 162, 164 may be expanded to temporarily engage the respective clinch members to lengthen or extend the connector length between the clinch members of the shunt rivet, e.g., to accommodate vessel separation distances, either prior to, during, or post implantation of the shunt rivet within the vessels. Alternatively, with members 162, 164 expanded, the connector length may be shortened between the clinch members.

The ability to adjust the length of the connector may allow for not only accommodating for the distance between the vessels, but also to "fine-tune" a flow rate of the blood through the shunt rivet to achieve a desired therapeutic result and/or to mitigate any side effects of the fistula. Moreover, although the adjustment to the shunt rivet may be done intra-operatively in vivo, adjustments may also be performed prior to insertion within the patient body. Moreover, an electronic or mechanical gauge or markers (such as visual markings or radio-opaque markers) may be integrated with the instrument 160 to provide feedback to the user as to the length that the shunt rivet is shortened or lengthened.

Figure 37:
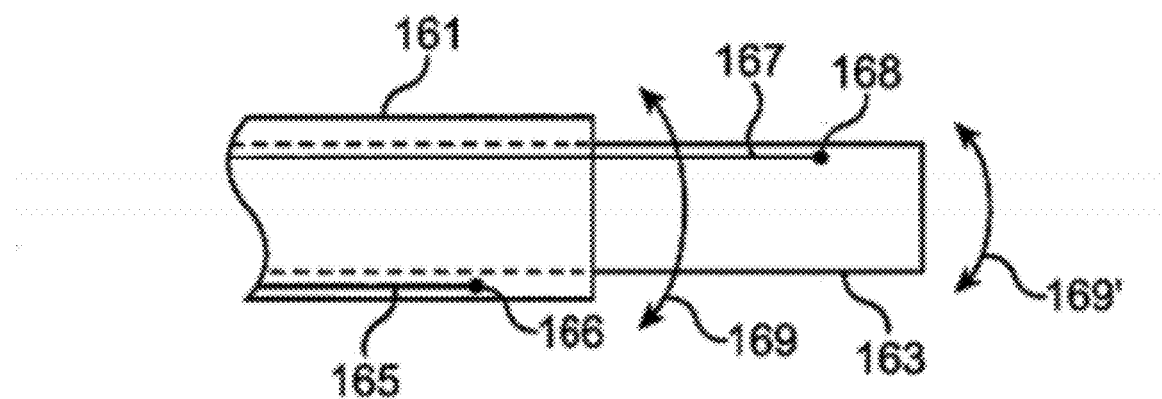
FIG. 37 shows a side view of another variation of an instrument which may be used to adjust an angle of the shunt rivet with respect to the vessels.
Figure 38:
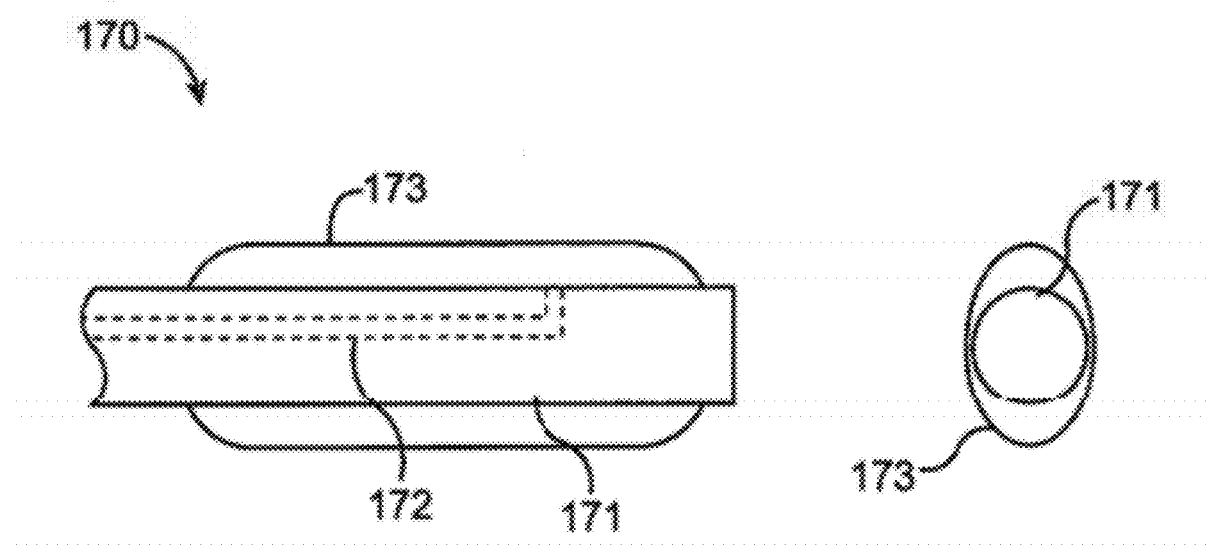
FIG. 38 shows side and end views, respectively, of another variation of an instrument having an inflatable balloon which may be used to adjust a cross-sectional area of the shunt rivet to adjust the flow rate between the vessels.

An example of another instrument which may be used to adjust an angle of the shunt rivet with respect to the vessels is shown in FIG. 37. As above, an inner sliding core 163 may be translatably positioned within outer sheath 161. A pull wire 165 may have a fixation point 166 near or at a distal end of sheath 161 and may be routed through outer sheath 161 and articulated 169 to adjust an angle of outer sheath 161 with respect to a longitudinal axis of sheath 161. Likewise, inner core 163 may also have a separate pullwire 167 with a fixation point 168 near or at a distal end of inner core 163 to adjust 169' its angle with respect to a longitudinal axis of inner core 163. Sliding core 163 and outer sheath 161 may both be articulated independently of one another to create multiple bending configurations. In this manner, a shunt rivet disposed within outer sheath 161 and/or upon sliding core 163 may be bent or curved into various configurations by the forces imparted upon the shunt rivet to adjust its angle with respect to the clinch members and vessels.

Such an instrument may be utilized to adjust not only an angle of, e.g., connectors between the clinch members, but also the hinge or flange 111 as well as other portions of the shunt rivet variations described herein. Moreover, the instrument may be utilized to plastically deform the portions of the shunt rivet. One or more radio-opaque markers may be included on the instrument to visually indicate an angle of the instrument. An additional and/or alternative variation may further include an instrument which is used to deform the tissue neighboring the fistula site in the same manner as adjusting angles, distances, etc., of the shunt rivet. The shunt rivet may also be plastically deformed or it may be simply elastically deformed to accommodate the tissue shape changes. Additionally, the instrument may further include a mechanical or electronic gauge to indicate the degree of force imparted on the shunt rivet as well as relaying other information during or post deployment.

Yet another feature of a deployment instrument is shown in the partial cross-sectional side and end views, respectively, in FIG. 38. As shown, inflatable end effector 170 may include an inflation balloon 173 in fluid communication with an inflation lumen 172 which is disposed near or at a distal end of a delivery shaft 171. A shunt rivet may be disposed proximate to, upon, or distal to inflation balloon 173 in its deflated state for delivery into the vessels. Prior to, during, or post deployment of the shunt rivet into the vessels, inflation balloon 173 may be inflated to adjust a cross-sectional area of the shunt rivet to adjust the flow rate between the vessels, e.g., up to 5 mm or more diameter and as described above in the shunt rivet variations. Inflation balloon 173 may be configured to have a circular cross-sectional area such that expansion within the shunt rivet may adjust the shunt to have a corresponding circular cross-sectional area. Alternative variations of the inflation balloon 173 may include balloons having non-circular cross sections, e.g., such as an oval cross section with adjustable major and/or minor axes, as shown in the end view of FIG. 38, to optionally adjust a shunt rivet cross section accordingly. Other non-circular cross-sectional areas may be utilized, e.g., polygon, trapezoid, triangle, rhombus, rectangle, square, parallelogram, etc., to optimize a flow through the fistula and to vary or optimize an effective flow diameter through the shunt rivet and between the interconnected vessels.

Figure 39:
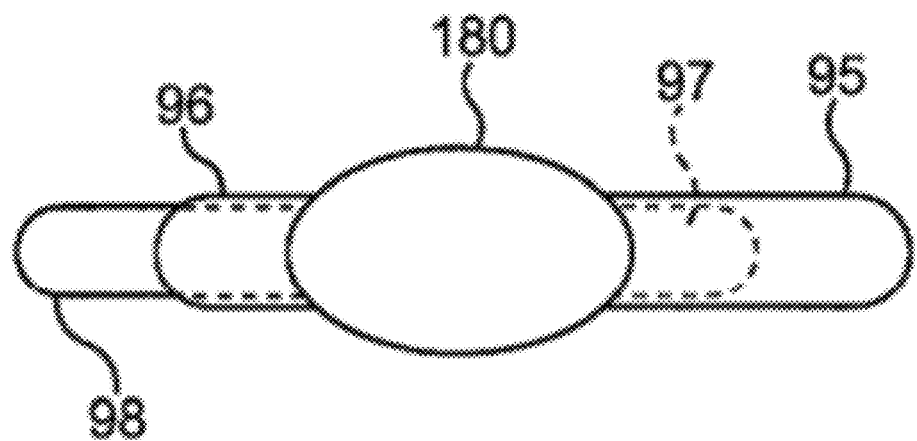
FIG. 39 shows a top view of a shunt rivet having an oval cross-sectional area which may be optionally adjusted.
Figure 40:
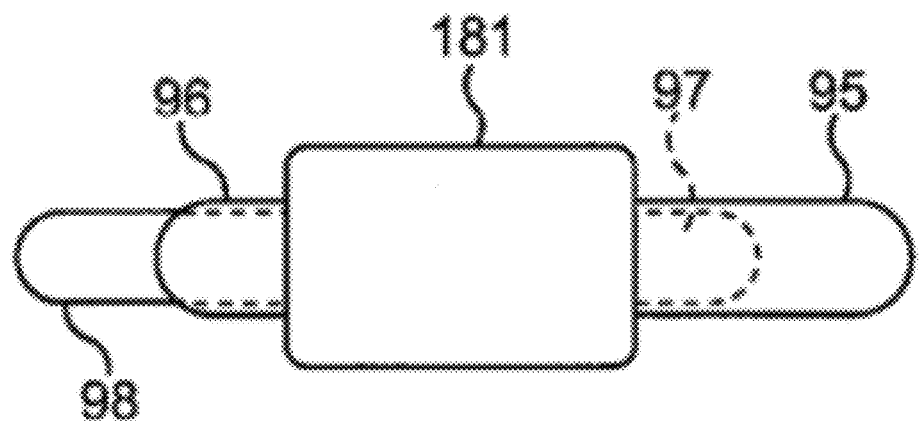
FIG. 40 shows a top view of another shunt rivet having a rectangular cross-sectional area.

FIG. 39 illustrates a top view of a shunt rivet having an example of an oval cross-sectional area 180, which may be optionally adjusted via the one or more instruments above. Another non-circular cross-sectional area is illustrated in FIG. 40, which shows a top view of a shunt rivet having a rectangular cross-sectional area 181. As mentioned, other non-circular cross-sectional areas (e.g., polygon, trapezoid, triangle, rhombus, rectangle, square, parallelogram, etc.) may be utilized to optimize flow conditions and/or therapeutic results for implantation between the vessels, as desired.

The devices described above may be provided with coatings or additional structures which serve as matrices for various therapeutic compounds. Drug eluting coatings, additional drug eluting strut members, drug eluting membranes surrounding the central section or drug eluting masses filling the cells of the device may be added to the devices. For the aortocaval application and the arterio-venous application, therapeutic agents such as heparin and other anti-coagulants and paclitaxol, rapamycin (Sirolumis™), everolimus and other anti-stenotic compounds can be applied to the stent in polymer matrices which permit elution of these drugs over a period of time ranging from several hours to several months after implantation. Polymers such as polyurethane can be used as the matrix.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims.

What is claimed is:

1. A method for creating an intravascular connection, comprising:

advancing an intravascular connector through a first vessel, the intravascular connector having a first pair of clinch members comprising a first member and an apposed second member and a second pair of clinch members opposite from the first pair of clinch members and also comprising a first member and an apposed second member;

introducing the second member of the first pair and the first member of the second pair into a second vessel from the first vessel such that the respective members deploy into contact against an inner wall of the second vessel; and deploying the first member of the first pair and the second member of the second pair into contact against an inner wall of the first vessel, wherein the first and second pairs of clinch members have a deployed configuration longitudinally disposed relative to contiguous portions of the first and second vessels such that the first and second pairs of clinch members are biased to close upon the contiguous parallel portions, wherein the first member of the first and second pair of clinch members each have a length less than each second member of the first and second pair of clinch members such that each first member is deployed on opposite ends of the connector within the first and second vessels, respectively, and each individual clinch member is deployable sequentially in a predetermined order within the first vessel and second vessel, and wherein each first member is sized to arc entirely within each respective vessel into its deployed position when each second member contacts each respective vessel wall.

2. The method of claim 1 wherein advancing an intravascular connector comprises advancing the connector within an outer sheath.

3. The method of claim 1 wherein prior to introducing, intravascularly crossing a guidewire from the first vessel into the second vessel such that the guidewire is disposed within the first and second vessels.

4. The method of claim 3 wherein introducing comprises advancing the intravascular connector at least partially from the first vessel and into the second vessel over or along the guidewire.

5. The method of claim 1 wherein introducing comprises releasing the first member of the second pair in an arc contained within the second vessel into contact against the inner wall of the second vessel.

6. The method of claim 1 wherein deploying comprises releasing the first member of the first pair in an arc contained within the first vessel into contact against the inner wall of the first vessel.

7. The method of claim 1 further comprising adjusting a physical parameter of the intravascular connector to modify a flow rate between the first and second vessels through the connector.

8. The method of claim 7 wherein adjusting a physical parameter comprises modifying a configuration of the intravascular connector via break-away, frangible, or deformable segments comprising at least a portion of the connector.

9. The method of claim 7 wherein adjusting a physical parameter comprises adjusting a cross-sectional area of the intravascular connector to adjust the flow rate therethrough.

10. The method of claim 7 wherein adjusting a physical parameter comprises adjusting a lumen length of the intravascular connector between the first and second vessels.

11. The method of claim 7 wherein adjusting a physical parameter comprises adjusting an angle of the intravascular connector extending between the first and second vessels.

12. The method of claim 1 further comprising deploying at least a third pair of clinch members having a deployed configuration transverse to the first and second pairs such that the third pair of clinch members are biased to exert a nominal pressure on circumferentially spaced points on side walls of the first and second vessels.

* * * * *